US012797188B2

(12) United States Patent
Korin et al.

(10) Patent No.: US 12,797,188 B2
(45) Date of Patent: Nov. 17, 2026

(54) PROSTHETIC HEART VALVE FOR MITIGATING STAGNATION

(71) Applicant: TECHNION RESEARCH & DEVELOPMENT FOUNDATION LIMITED, Haifa (IL)

(72) Inventors: Netanel Korin, Haifa (IL); Yevgeniy Kreinin, Haifa (IL); Mark Epshtein, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 815 days.

(21) Appl. No.: 18/135,134

(22) Filed: Apr. 15, 2023

(65) Prior Publication Data

US 2023/0255753 A1 Aug. 17, 2023

Related U.S. Application Data

(63) Continuation of application No. PCT/IL2021/051257, filed on Oct. 24, 2021.

(60) Provisional application No. 63/105,302, filed on Oct. 25, 2020.

(51) Int. Cl.
*A61F 2/24* (2006.01)

(52) U.S. Cl.
CPC .......... *A61F 2/2403* (2013.01); *A61F 2/2412* (2013.01)

(58) Field of Classification Search
CPC ............................ A61F 2/2403; A61F 2/2412
See application file for complete search history.

(56) References Cited

U.S. PATENT DOCUMENTS 12,440,333 B1 * 10/2025 Schneider ............ A61F 2/2418
2002/0183840 A1 * 12/2002 Lapeyre ............... A61F 2/2403 623/2.22
2007/0168022 A1 7/2007 Eldridge
2017/0196686 A1 * 7/2017 Tien ..................... A61F 2/2415
(Continued)

OTHER PUBLICATIONS

Dangas et al (2016) Prosthetic Heart Valve Thrombosis, Journal of the American College of Cardiology, 68 (24):2670-2689. doi: 10.1016/j.jacc.2016.09.958. PMID: 27978952.
(Continued)

*Primary Examiner* — Suzette J Gherbi
(74) *Attorney, Agent, or Firm* — The Roy Gross Law Firm, LLC; Roy D. Gross

(57) ABSTRACT

A prosthetic heart valve including a valve housing configured to be positioned adjacent to a heart valve annulus, one or more flaps moveably coupled to the valve housing, a passage defined by an inner surface of at least one of the valve housing and the one or more flaps, wherein the passage is configured to facilitate blood flow therethrough along a longitudinal axis thereof, from an inflow side to an outflow side of the valve, one or more openings through the inner surface located such that at an open position of the heart valve, a portion of the blood flow flowing along the longitudinal axis of the passage is redirected from the passage through the one or more openings, wherein the direction of the redirected blood flow has a component that is normal to the longitudinal axis of the passage, thereby mitigating stagnation of the blood flow and thus mitigating a risk of blood clots formation.

13 Claims, 18 Drawing Sheets
(8 of 18 Drawing Sheet(s) Filed in Color)

(56) References Cited

U.S. PATENT DOCUMENTS

| | | | | |
|---|---|---|---|---|
| 2018/0353293 | A1 | 12/2018 | Colavito et al. | |
| 2021/0121290 | A1* | 4/2021 | Alkhatib | A61F 2/2412 |
| 2021/0338419 | A1* | 11/2021 | Gifford, III | A61F 2/2418 |
| 2022/0218469 | A1* | 7/2022 | Straubinger | A61F 2/2412 |
| 2023/0149162 | A1* | 5/2023 | Gurovich | A61F 2/2418 623/2.17 |
| 2023/0218391 | A1* | 7/2023 | Dass | A61F 2/2418 623/2.18 |
| 2024/0033075 | A1* | 2/2024 | Amerio | A61F 2/2403 |
| 2024/0065830 | A1* | 2/2024 | Cohen | A61F 2/2403 |
| 2024/0238090 | A1* | 7/2024 | Zhu | A61M 25/0136 |
| 2025/0114198 | A1* | 4/2025 | Zamani | A61F 2/2409 |
| 2025/0161034 | A1* | 5/2025 | Moore | A61F 2/2418 |
| 2025/0255718 | A1* | 8/2025 | Christianson | A61F 2/2409 |
| 2025/0302614 | A1* | 10/2025 | VanEvery | A61F 2/2418 |

OTHER PUBLICATIONS

Bluestein et al (2004) Flow-Induced Platelet Activation in a Mechanical Heart Valve, The Journal of Valve Disease, 13(3): 501-8. PMID: 15222299.

Yin et al (2004) Flow-Induced Platelet Activation in Bileaflet and Monoleaflet Mechanical Heart Valves, Annals of Biomedical Engineering, 32(8):1058-1066. DOI: 10.1114/b:abme.0000036642.21895.3f.

PCT International Search Report for International Application No. PCT/IL2021/051257, mailed Feb. 9, 2022, 4pp.

PCT Written Opinion for International Application No. PCT/IL2021/051257, mailed Feb. 10, 2022, 7pp.

PCT International Preliminary Report on Patentability for International Application No. PCT/IL2021/051257, issued Apr. 13, 2023, 8pp.

* cited by examiner

1450

1400

PROSTHETIC HEART VALVE FOR MITIGATING STAGNATION

CROSS REFERENCE TO RELATED APPLICATIONS

This application is a Bypass Continuation of PCT Patent Application No. PCT/IL2021/051257 having International filing date of Oct. 24, 2021, which claims the benefit of priority of U.S. Provisional Patent Application No. 63/105,302, filed Oct. 25, 2020, the contents of which are all incorporated herein by reference in their entirety.

FIELD OF THE INVENTION

The present invention, in some embodiments thereof, relates to heart valves configured to mitigate stagnation and, more particularly, but not exclusively, to heart valves including a plurality of openings.

BACKGROUND

Valvular heart disease affects over 100 million people worldwide and is associated with significant morbidity and mortality. More specifically, in recent years, the prevalence of degenerative valve diseases has increased. Currently, surgical valve replacement is the standard of care for treatment of valvular heart disease in patients at low and intermediate risk for surgery. There are two common types of prosthetic heart valves, differentiated by the material of the leaflet of the heart valve: mechanical and bioprosthetic. The mechanical heart valves are usually more thrombogenic, however, commonly last longer and are more durable than bioprosthetic heart valves. Bioprosthetic heart valves are less thrombogenic than the mechanical heart valves, but usually last less time and are less durable than the mechanical heart valves. There is thus an unmet need for improved prosthetic heart valves.

SUMMARY

According to some embodiments of the present invention there is provided a prosthetic heart valve, including: a valve housing configured to be positioned adjacent to a heart valve annulus, one or more flaps moveably coupled to the valve housing, a passage defined by an inner surface of at least one of the valve housing and the one or more flaps, wherein the passage is configured to facilitate blood flow therethrough along a longitudinal axis thereof, from an inflow side to an outflow side of the valve, one or more openings through the inner surface located such that at an open position of the heart valve, a portion of the blood flow flowing along the longitudinal axis of the passage is redirected from the passage through the one or more openings, wherein the direction of the redirected blood flow has a component that is normal to the longitudinal axis of the passage, thereby mitigating stagnation of the blood flow and thus mitigating a risk of blood clots formation.

According to some embodiments of the present invention there is provided a prosthetic heart valve, including: a valve housing configured to be positioned adjacent to a heart valve annulus, one or more flaps moveably coupled to the valve housing, a passage defined by an inner surface of at least one of the valve housing and the one or more flaps, wherein the passage is configured to facilitate blood flow therethrough along a longitudinal axis thereof, from an inflow side to an outflow side of the valve, one or more openings through the inner surface located such that at an open position of the heart valve, a portion of the blood flow is redirected away from a main blood flow flowing through the passage along a longitudinal axis thereof, thereby reducing the volumetric flow rate of the main flow, wherein the one or more openings are sized and positioned such that the volumetric flow rate is below a predetermined threshold value associated with fluttering of the one or more flaps throughout a heart cycle.

According to some embodiments of the present invention there is provided a method for mitigating stagnation of blood flow through a prosthetic heart valve, including: implanting a prosthetic heart valve including a valve housing configured to be positioned adjacent to a heart valve annulus, one or more flaps moveably coupled to the valve housing, a passage defined by an inner surface of at least one of the valve housing and the one or more flaps, wherein the passage is configured to facilitate blood flow therethrough along a longitudinal axis thereof, from an inflow side to an outflow side of the valve, one or more openings through the inner surface located such that at an open position of the heart valve, a portion of the blood flow flowing along the longitudinal axis of the passage is redirected from the passage through the one or more openings, wherein the direction of the redirected blood flow has a component that is normal to the longitudinal axis of the passage, thereby mitigating stagnation of the blood flow and thus mitigating a risk of blood clots formation.

According to some embodiments of the present invention there is provided a method for preventing fluttering of the flaps of a prosthetic heart valve, including: implanting a prosthetic heart valve including a valve housing configured to be positioned adjacent to a heart valve annulus, one or more flaps moveably coupled to the valve housing, a passage defined by an inner surface of at least one of the valve housing and the one or more flaps, wherein the passage is configured to facilitate blood flow therethrough along a longitudinal axis thereof, from an inflow side to an outflow side of the valve, one or more openings through the inner surface located such that at an open position of the heart valve, a portion of the blood flow flowing along the longitudinal axis of the passage is redirected from the passage through the one or more openings, wherein the direction of the redirected blood flow has a component that is normal to the longitudinal axis of the passage, thereby mitigating stagnation of the blood flow and thus mitigating a risk of blood clots formation.

According to some embodiments, the one or more openings through the inner surface are located such that at an open position of the heart valve, a portion of the blood flow is redirected from the passage, through the one or more openings, in a plurality of directions with a normal component to the longitudinal axis of the passage.

According to some embodiments, the inner surface including the one or more openings is part of the housing.

According to some embodiments, the inner surface including the one or more openings is part of the one or more flaps.

According to some embodiments, the valve housing includes a flange circumferentially extending from the outflow side of the heart valve and wherein the flange includes the inner surface including the one or more openings.

According to some embodiments, two or more of the one or more openings are positioned at opposing portions of the heart valve.

According to some embodiments, at a closed position of the heart valve, the flaps are positioned as to restrict the entering blood flow from exiting the heart valve through the one or more openings.

According to some embodiments, the prosthetic heart valve includes one or more sub-passages located between the one or more openings and the outflow side of the heart valve, wherein the one or more of the sub-passages are structured to further redirect a blood flow from the one or more openings.

According to some embodiments, the flaps are bioprosthetic\ bioprosthetic-like. According to some embodiments, the one or more openings are positioned such that at an open position, a portion of the blood flow is redirected from the passage to a cavity formed between a heart tissue wall surface and the passage.

According to some embodiments, the one or more openings are positioned such that the blood flow is directed laminarly in a plurality of directions, thereby flushing one or more surfaced of the valve housing and/or one or more flaps.

According to some embodiments, the one or more openings are positioned such as to facilitate backflow of blood through the one or more openings and thereby facilitate flushing blood through the one or more openings when the flaps are at least partially closed.

According to some embodiments, the one or more openings are sized and positioned such as to define a predetermined flow field surrounding the heart valve during each phase of the heart cycle.

According to some embodiments, the prosthetic heart valve includes at least one support member positioned along at least a portion of the one or more flaps, wherein an elasticity of the support member is lower than an elasticity of the one or more flaps.

According to some embodiments, the support member is positioned along at least a section of a perimeter of the one or more flaps.

According to some embodiments, the support member is positioned along a length of the one or more flaps essentially parallel to the longitudinal axis of the passage.

According to some embodiments, the prosthetic heart valve further includes at least one tether coupled at a first end thereof to at least one flap.

According to some embodiments, a second end of the tether is configured to couple to a cardiac tissue of the subject.

According to some embodiments, a second end of the tether is coupled to a second flap.

According to some embodiments, the one or more openings are sized and positioned in the inner wall such that the redirected blood flow has a Reynolds number below a predetermined threshold value associated with preventing turbulence and thereby preventing or mitigating fluttering of the one or more flaps.

According to some embodiments, the one or more openings are sized and positioned in the inner wall such that a main blood flow and the redirected blood flow have a Reynolds number below a predetermined threshold value throughout the heart cycle.

According to some embodiments, the threshold value ranges between 100 and 200.

According to some embodiments, the one or more openings are sized and positioned in the inner wall such that a shear stress accumulated on the valve housing is below a predetermined threshold value associated with platelet shear activation and/or hemolysis.

According to some embodiments, the threshold value ranges between 250 to 350 dyne/cm$^2$.

BRIEF DESCRIPTION OF THE FIGURES

The patent or application file contains at least one drawing executed in color. Copies of this patent or patent application publication with color drawing(s) will be provided by the Office upon request and payment of the necessary fee.

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1A:
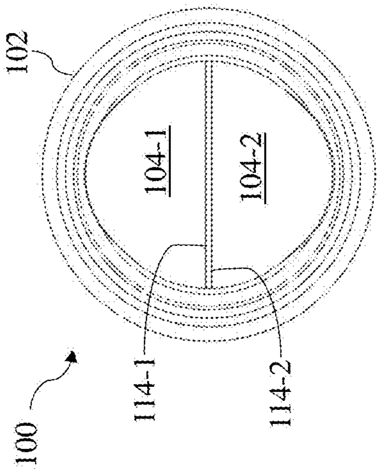
FIG. 1A, FIG. 1B, and FIG. 1C are top view, side view, and perspective view simplified illustrations of an exemplary prosthetic heart valve, respectively, at a closed position of the heart valve, in accordance with some embodiments of the present invention.

According to an aspect of some embodiments of the present invention there is provided a prosthetic heart valve configured to mitigate or eliminate the stagnation of blood flow surrounding the prosthetic heart valve.

According to some embodiments of the present invention there is provided a prosthetic heart valve configured to mitigate stagnation by redirecting a portion of the main blood flow to one or more directions including a component essentially normal to the main blood flow. According to some embodiments of the present invention there is provided a prosthetic heart valve configured to promote laminar flow of the blood stream entering and/or exiting the heart valve, and/or reduce turbulence-induced fluttering of the flaps of the heart valve. According to some embodiments of the present invention there is provided a prosthetic heart valve structured such that when positioned adjacent to a heart valve annulus, the shear stress that develops within an inner wall of the heart valve is below a threshold value associated with platelet shear activation and hemolysis.

According to some embodiments, the prosthetic heart valve includes a valve housing configured to be positioned adjacent to a heart valve annulus. According to some embodiments, the prosthetic heart valve includes one or more flaps moveably coupled to the valve housing. According to some embodiments, the prosthetic heart valve includes a passage defined by an inner surface of at least one of the valve housing and the one or more flaps, wherein the passage is configured to facilitate blood flow therethrough along a longitudinal axis thereof, from an inflow side to an outflow side of the valve. According to some embodiments, the prosthetic heart valve includes one or more openings through the inner surface located such that at an open position of the heart valve, a portion of the blood flow flowing along the longitudinal axis of the passage is redirected from the passage through the one or more openings, wherein the direction of the redirected blood flow has a component essentially normal to the longitudinal axis of the passage, thereby mitigating stagnation of the blood flow and thus mitigating a risk of blood clots formation.

According to some embodiments of the present invention there is provided a prosthetic heart valve configured to mitigate stagnation by flushing one or more walls of the heart valve. According to some embodiments, the prosthetic heart valve includes one or more openings at specific locations and/or orientations in relation to the passage, such that the main blood flow entering the heart valve is actively redirected, thereby flushing one or more portions of the prosthetic heart valve. According to some embodiments, flushing of the one or more walls of the heart valve includes redirecting one or more blood streams towards the one or more walls.

According to some embodiments, the heart valve is structured such that entering blood flow is manipulated through a predetermined flow field. According to some embodiments, the predetermined flow field includes laminar flow. According to some embodiments, the predetermined flow field flushes one or more surfaces of the heart valve. According to some embodiments, the predetermined flow field flushes different portion of the heart valves at different portion of the cycle.

According to some embodiments of the present disclosure there is provided a prosthetic heart valve configured to reduce fluttering of the flaps of the heart valve by reducing the volumetric flow rate of the main blood flow. According to some embodiments, the one or more openings of the heart valves are positioned such that a portion of the main blood flow diverges from the main flow, thereby reducing the volumetric flow rate of the main flow. According to some embodiments, the blood streams which diverge from the main blood flow are redirected by the one or more openings and/or flaps of the heart valve.

A potential advantage of lowering the volumetric flow rate of the main flow is that lowering of the volumetric flow rate of the main flow decreases and/or prevents a fluttering of the flaps of the heart valve.

A potential advantage of lowering the volumetric flow rate of the main flow is that lowering of the volumetric flow rate of the main flow increases the stability of the position of the housing of the heart valve in the heart of the subject.

According to some embodiments of the present disclosure there is provided a prosthetic heart valve configured to reduce fluttering of the flaps of the heart valve by preventing turbulent flow and/or promoting laminar flow of blood entering and/or exiting the heart valve. According to some embodiments, the heart valve includes one or more openings which are configured to redirect the blood flow such that the local Reynolds number, in both the redirection path and the main opening, is below a predetermined threshold value throughout the heart cycle. According to some embodiments, the Reynolds number predetermined threshold value is associated with actively preventing turbulence and thereby preventing fluttering of the one or more flaps. According to some embodiments, the Reynolds number predetermined threshold value is under 2000.

According to some embodiments, the prosthetic heart valve is configured to redirect two or more opposing blood streams laminarly and in opposing directions such that the Reynolds number associated with one or more portions of the flow field surrounding the heart valve is below a predetermined threshold value.

A potential advantage of controlling the flow field surrounding the heart valve and/or preventing turbulent blood flow surrounding the heart valve is in that the heart valve may be stably positioned in relation to prosthetic heart valves having no openings.

A potential advantage of the prosthetic heart valve including one or more openings is in that the flow field surrounding the heart valve and resulting from the redirection of the blood flow though the one or more openings prevents interruption of blood flow and/or stasis in areas surrounding the prosthetic heart valve.

According to some embodiments of the present disclosure there is provided a heart valve including one or more openings sized and shaped such that the shear stress of that develops within the inner wall of the passage is below a threshold value associated with platelet shear activation and/or hemolysis. According to some embodiments, the one or more openings are sized and positioned in relation to the passage such that a shear stress accumulated on the valve housing is below a predetermined threshold value associated with platelet shear activation and/or hemolysis. According to some embodiments, the threshold value is less than or equal to 350 dyne/cm$^2$.

According to some embodiments of the present disclosure there is provided a heart valve including a passage configured to facilitate blood flow from an inflow side to an outflow side of the heart valve, and at least one sub-passage defining one or more openings configured to redirect at least a portion of the blood flow through the one or more openings. According to some embodiments, the one or more sub-passages are configured to reduce the volumetric flow rate of the blood entering the heart valve. According to some embodiments, the one or more sub-passages are configured to control the flow field surrounding the heart valve such that the flow field includes a predetermined Reynolds number range.

According to some embodiments of the present disclosure there is provided a prosthetic heart valve including one or more openings, wherein the openings were added to and/or carved out of a prosthetic heart valve.

According to some embodiments of the present disclosure there is provided a prosthetic heart valve including one or more tethers configured to couple at one end thereof to one or more of the flaps. According to some embodiments, the tether is coupled to a portion and/or one layer of a plurality of layers of the one or more flaps. According to some embodiments, the tether is couplable at a second end thereof to one or more of a second flap, the valve housing, and cardiac tissue of the subject.

A potential advantage of the prosthetic heart valve including one or more tethers coupled to the one or more flaps is in that layers of the one or more flaps which define the one or more openings may be openable in a radially inward direction. According to some embodiments, the one or more tethers may pull a portion of the flap towards a center of the passage of the heart valve, thereby increasing the size of the one or more openings.

A potential advantage of the one or more flaps being coupled to the cardiac tissue of the subject is in that the opening of the one or more openings is synchronized with the heart cycle. According to some embodiments, having the one or more tethers coupled to the flap near an opening within the flap enables the controlled closing of the openings, in relation to the opening and closing of one or more flaps that are not coupled to tethers, during the heart cycle. According to some embodiments, having the one or more tethers coupled to the flap near an opening within the flap enables the independent closing of the openings, in relation to the opening and closing of one or more flaps that are not coupled to tethers, during the heart cycle.

According to some embodiments, and as described in greater detail elsewhere herein, the one or more openings may be one or more sub-passages.

Figure 1B:
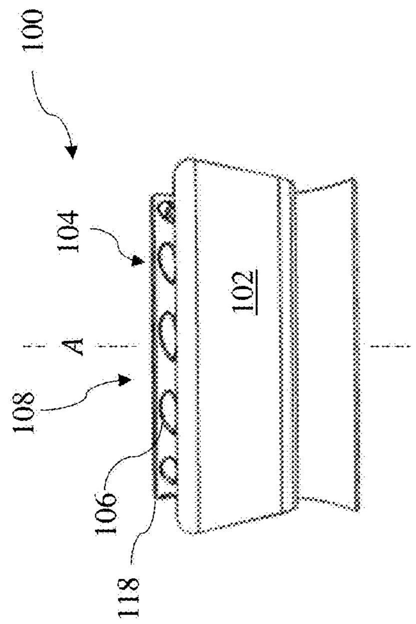
Figure 1C:
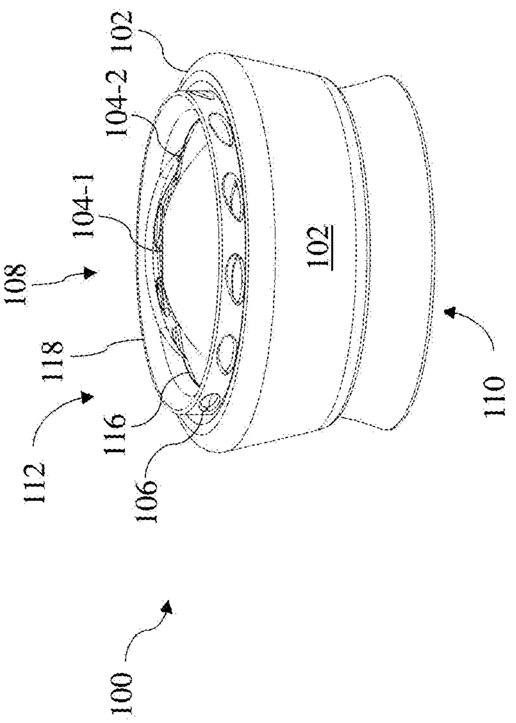
Figure 1D:
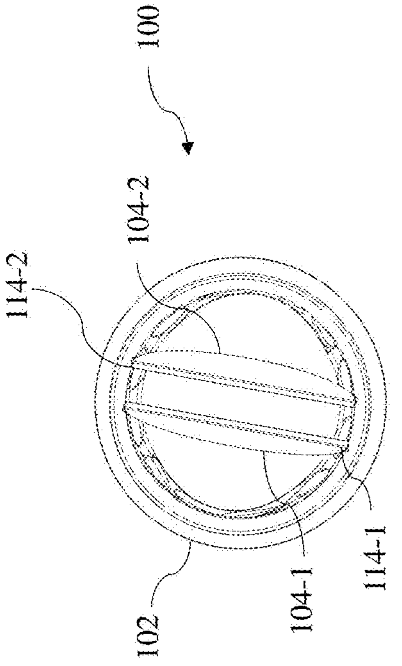
FIG. 1D, FIG. 1E and FIG. 1F are bottom view and perspective view simplified illustrations of the exemplary prosthetic heart valve (of FIGS. 1A-C) at an open position, in accordance with some embodiments of the present invention.
Figure 1F:
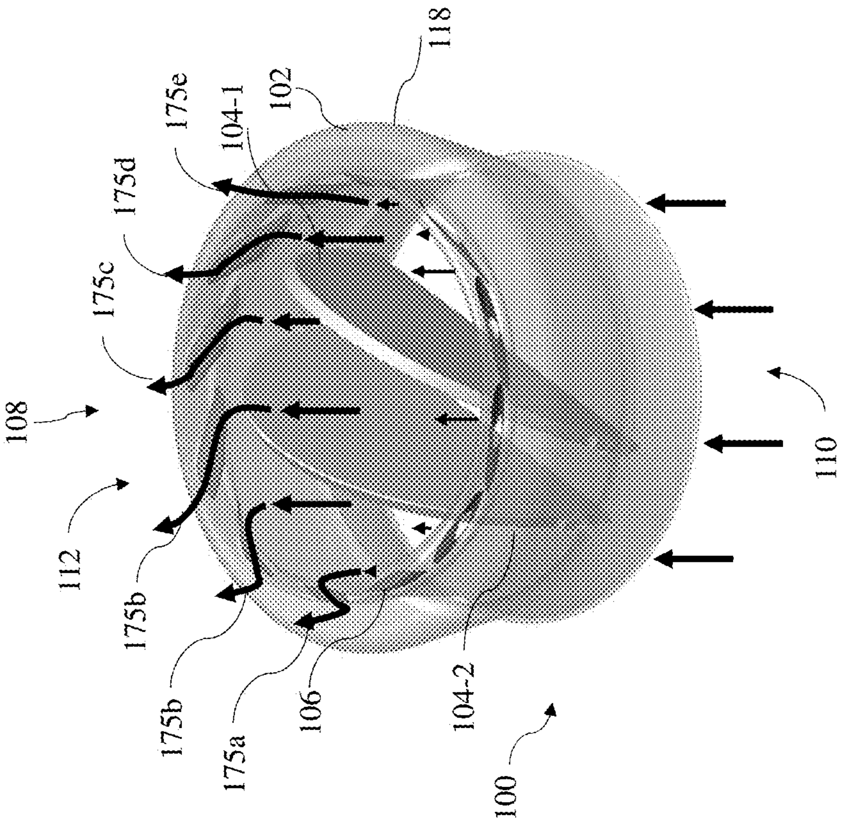
Figure 1E:
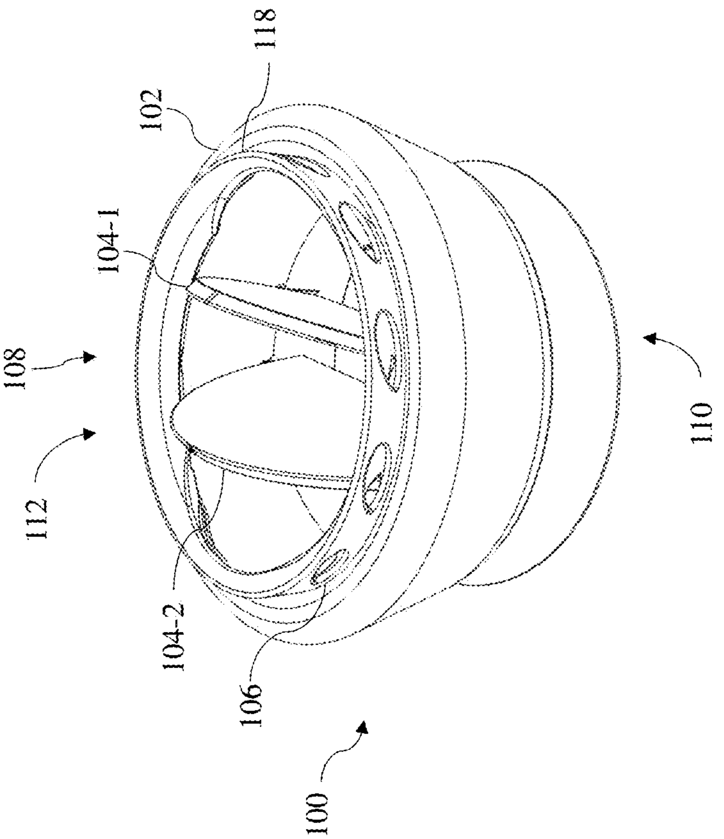

Reference is made to FIG. 1A, FIG. 1B, and FIG. 1C, which are top view, side view, and perspective view simplified illustrations of an exemplary prosthetic heart valve, respectively, at a closed position of the heart valve, in accordance with some embodiments of the present invention, to FIG. 1D, FIG. 1E, and FIG. 1F, which are bottom view and perspective view simplified illustrations of the exemplary prosthetic heart valve (of FIGS. 1A-C) at an open position, in accordance with some embodiments of the present invention, and to FIG. 2A, FIG. 2B, FIG. 2C, and FIG. 2D, which are top view, side view, perspective view, and bottom view simplified illustrations of an exemplary prosthetic heart valve, respectively, in accordance with some embodiments of the present invention.

According to some embodiments, the prosthetic heart valve 100/200 includes a mechanical heart valve portion. According to some embodiments, the prosthetic heart valve 100/200 includes a bioprosthetic or bioprosthetic-like heart valve portion. According to some embodiments, the prosthetic heart valve 100/200 includes a combination of one or more mechanical portions and one or more bioprosthetic portions. According to some embodiments, the prosthetic heart valve 100/200 includes a valve housing 102/202 coupled to one or more flaps 104-2/104-2/201-1/204-2/204-3 (referred to hereinafter as flaps 104/204). According to some embodiments, the valve housing 102/202 and/or the one or more flaps 104/204 define a passage 108/208 configured to facilitate blood from an inflow side 110/210 of the heart valve 100/200 to an outflow side 112/212 of the heart valve 100/200.

According to some embodiments, the valve housing 102/202 includes a support frame configured to position adjacent to a heart valve annulus of a subject. According to some embodiments, the valve housing 102/202 is rigid, semi-rigid, and/or flexible. According to some embodiments, the valve housing 102/202 includes an annular shape, a C-shape, or a D-shape. According to some embodiments, the valve housing 102/202 includes an adjustable and/or malleable shape. According to some embodiments, the valve housing 102/202 includes an elongated tubular shape. According to some embodiments, the valve housing 102/202 is hollow.

According to some embodiments, the one or more flaps 104/204 are configured to couple to the valve housing 102/202. According to some embodiments, such as depicted in FIG. 1A, FIG. 1B, FIG. 1C, and FIG. 1D, the one or more flaps 104 are coupled to the valve housing 102 at the outflow side 112 thereof. According to some embodiments, the one or more flaps 104 are coupled to the valve housing via one or more axes 114-1/114-2 (referend to hereinafter as axes 114). According to some embodiments, the one or more flaps are rotatable about the one or more axes 114. According to some embodiments, the one or more flaps 104 are sized such that at a closed position of the prosthetic heart valve, such as depicted in FIG. 1A, the one or more flaps 104 extend from the one or more exes 114 to a circumference of the valve housing 102.

According to some embodiments, the one or more axes 114 are positioned along a geometrical cord of the circumference of the valve housing 102. According to some embodiments, the one or more axes 114 is essentially normal to the longitudinal axis (A) of the passage 108. According to some embodiments, the one or more axes 114 is straight, convex, or concave. According to some embodiments, the one or more axes 114 is positioned within the prosthetic heart valve 100. and/or extend between one or more inner walls of the prosthetic heart valve 100. According to some embodiments, the one or more axes 114 traverse the passage 108 of the prosthetic heart valve 100.

According to some embodiments, the one or more flaps 104 are configured to rotate about the one of more axes 114 such that at an open position of the prosthetic heart valve 100, the one or more flaps 104 are drawn closer together in relation to the positions of the one or more flaps 104 at a closed position of the prosthetic heart valve 100.

According to some embodiments, the one or more flaps 104 are rigid, semi-rigid and/or flexible. According to some embodiments, the elasticity of the one or more flaps 104 varies along a length thereof. According to some embodiments, such as depicted in FIG. 2A, FIG. 2B, FIG. 2C, and FIG. 2D, the one or more flaps 204 are coupled to the valve housing 202 at the inflow side 210 thereof. According to some embodiments, the one or more flaps 204 extend from the valve housing 202 and/or an inner wall of the valve housing 202. According to some embodiments, the one or more flaps 204 are flexible and/or semi-rigid. According to some embodiments, the one or more flaps 204 are coupled to each other. According to some embodiments, the flaps 104/204 are bioprosthetic and/or bioprosthetic-like.

According to some embodiments, at an open position of the prosthetic heart valve 200, the one or more flaps 204 form an inner sheath within the valve housing 202. According to some embodiments, at a closed position of the prosthetic heart valve 200, the ends of the one or more flaps 204 are abutting. According to some embodiments, the one or more flaps 204 are sized and shaped such that at a closed position of the prosthetic heart valve 200, the one or more flaps 204 form a barrier within the passage 208 and/or across a cross section of the valve housing 202.

According to some embodiments, the passage 108/208 is defined by an inner wall 116/216 of at least one of the valve housing 102/202 and the one or more flaps 104/204. According to some embodiments, the passage 108/208 is configured to facilitate blood flow therethrough along a longitudinal axis (A)/(B) of the passage 108/208, from an inflow side 110/210 to an outflow side 112/212 of the prosthetic heart valve 100/200.

According to some embodiments, the passage 108 is defined by the inner wall 116 of the valve housing 102. According to some embodiments, the passage 208 is defined by the one or more flaps 204. According to some embodiments, the passage 108/208 is defined by the inner wall of the valve housing 102/202 and the one or more flaps 204.

According to some embodiments, the prosthetic heart valve 100/200 includes one or more openings 106/206 configured to redirect a portion of the main blood flow from the passage 108/208. According to some embodiments, the inner surface of the valve housing 102/202 includes the one or more openings 106/206. According to some embodiments, the one or more openings 106/206 are positioned through at least one of the inner wall 116/216 of the passage 108/208 and the one or more flaps 104/204. According to some embodiments, the one or more openings 106/206 are positioned through the inner wall 116/216 of the passage 108/208 and the one or more flaps 104/204.

According to some embodiments, the one or more openings 106/206 are positioned through a flange 118 of the prosthetic heart valve 100/200. According to some embodiments, at a closed position of the heart valve 100/200, the flaps 104/204 are positioned as to restrict the entering blood flow from exiting the heart valve 100/200 through the openings.

According to some embodiments, the one or more openings 106/206 are positioned such that at an open position of the heart valve 100/200, the blood flow is actively redirected through the opening from the main flow entering the inflow side 110/210 of the heart valve 100/200.

According to some embodiments, such as depicted in FIG. 1F and as described in greater detail elsewhere herein, the heart valve 100/200 may include one or more openings configured to direct the blood flow laterally. According to some embodiments, the lateral flow directed by the one or more openings may be lateral in relation to a cross-sectional plane of the passage 108/208 and/or a cross-sectional plane of the valve housing 102/202. According to some embodiments, the one or more openings may be configured to ensure sufficient lateral blood flow from (or through) the one or more openings and toward one or more stagnation areas (or cavities), such as depicted by arrows 175. According to some embodiments, the one or more stagnation areas may be areas located between the heart valve and the tissue wall. According to some embodiments, the stagnation area may be circumferential. According to some embodiments, the stagnation areas may be areas which are prone to stagnation of blood flow when using a heart valve that does not contain the one or more openings as described herein.

Advantageously, a heart valve including one or more openings may prevent the stagnation of blood flow within the stagnation areas (or cavities) by streamlining blood through the one or more openings. According to some embodiments, the one or more openings may be configured to redirect the flow laterally and ensure sufficient lateral flow therethrough. Thus, the one or more openings may prevent stagnation of the blood in the stagnation areas (or cavities) by generating circulation therethrough.

According to some embodiments, the one or more openings 106/206 are positioned at opposing portions of the heart valve 100/200. According to some embodiments, the one or more openings 106/206 encircle a perimeter of the heart valve. According to some embodiments, the one or more openings 106/206 extend along at least a portion of the perimeter of the heart valve 100/200. According to some embodiments, the one or more openings 106/206 extend along at least a portion of the perimeter of the valve housing 102/202.

According to some embodiments, the one or more openings 106/206 are positioned such that a back flow of blood enters the openings and thereby facilitates flushing through the one or more openings 106/206 when the one or more flaps 104/204 are partially closed. According to some embodiments, one or more openings 106/206 are positioned such that a back flow of blood enters the one or more openings 106/206 continuously throughout the heart cycle. According to some embodiments, the direction of the entering blood into the one or more openings 106/206 varies throughout the heart cycle.

Figure 3:
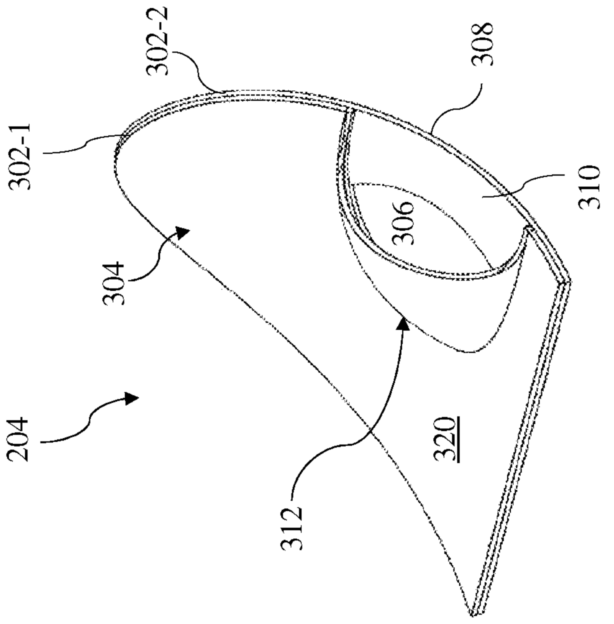
FIG. 3 is perspective view schematic illustration of an exemplary portion of a flap of a prosthetic heart valve, in accordance with some embodiments of the present invention.

Reference is made to FIG. 3, which is perspective view schematic illustration of an exemplary portion of a flap of a prosthetic heart valve, in accordance with some embodiments of the present invention.

According to some embodiments, the one or more flaps 204 include a plurality of layers 302-1/302-2 (referred to herein as layers 302). According to some embodiments, the thickness of the one or more flaps 204 is defined by the total thickness of the plurality of layers 302. According to some embodiments, each of the layers of the plurality of layers 302 varies in shape and thickness in relation to other layers 302 of the plurality of layers 302. According to some embodiments, the plurality of layers 302 are coupled to each other at one or more portions, such as portion 304 in FIG. 3. According to some embodiments, the plurality of layers 302 are separate at one or more portions, such as portion 308 in FIG. 3.

According to some embodiments, the openings 306 are formed between the plurality of layers 302 of the one or more flaps 204. According to some embodiments, the portion 308 including separate layers 302 includes a first section 310 and a second section 312 of the plurality of layers, wherein the first section 310 is separate from the second section 312. According to some embodiments, during implementation of the prosthetic heart valve 100/200, the position of at least one of the first section 310 and the second section 312 is changed such that blood flow is directed through an opening 306 formed therebetween.

A potential advantage of the one or more openings 306 being formed between the plurality of layers 302 is in that the total thickness of the one or more flaps 204 is larger than the thickness of the layers 302 defining the one or more openings 306. Advantageously, according to some embodiments the thickness of the first section 310 and/or second section 312 is smaller than the total thickness of the flaps 204 at portions in which the plurality of layers 302 are united. According to some embodiments, at least one of the first section 310 and the second section 312 includes a higher elasticity, a lower thickness, and/or lower hardness than the portions of the flap 204 in which the plurality of layers 302 are not separated.

According to some embodiments, the one or more openings 106/206/306 include a circular, oval, and/or polygonal shape. According to some embodiments, the shape of the one or more openings 106/206/306 is different and/or varies in relation to one or more other openings 106/206/306. According to some embodiments, the walls of the openings 106/206/306 are straight and/or curved. According to some embodiments, the edges of the openings 106/206/306 are curved and/or include no corners.

According to some embodiments, the one or more openings 106/206/306 include between 1 and 30 openings. According to some embodiments, the one or more openings extend along 10% to 100% of the perimeter of a portion of the prosthetic heart valve 100/200. According to some embodiments, the one or more openings 106/206/306 include an open area defined as the area bound by a perimeter of the openings 106/206/306. According to some embodiments, the one or more openings 106/206/306 include a total open area defined as the total area bound by the perimeters of all of the openings 106/206/306. According to some embodiments, during implementation, the one or more openings 106/206/306 are configured to open and/or close in response to hydrodynamic pressure gradients of the blood flow within the heart of the subject. According to some embodiments, the one or more openings 106/206/306 are sized and positioned such that a flow field surrounding the heart valve 100/200 is predetermined throughout the heart cycle.

According to some embodiments, the open area of the one or more openings 106/206/306 includes one or more planes essentially normal to the longitudinal axis (A)/(B) of the passage 108/208. According to some embodiments, the open area of the one or more openings 106/206/306 is configured such that the direction of the redirected blood flow has a component essentially normal to the longitudinal axis (A)/(B) of the passage 108/208. According to some embodiments, the ratio between the total open area and the length of the passage 108/208 is within a predetermined range of values. According to some embodiments, the ratio between the total size of the openings 106/206/306 and the length of the passage 108/208 cross section is larger than a predetermined ratio threshold. According to some embodiments, the ratio between the total open area and the length of the passage 108/208 is configured such that the flow field surrounding one or more portions of the prosthetic heart valve 100/200 is configured to mitigate stagnation of the blood flow and thus mitigate a risk of blood clots formation.

Figures 2A, 2B, 2C, 2D:
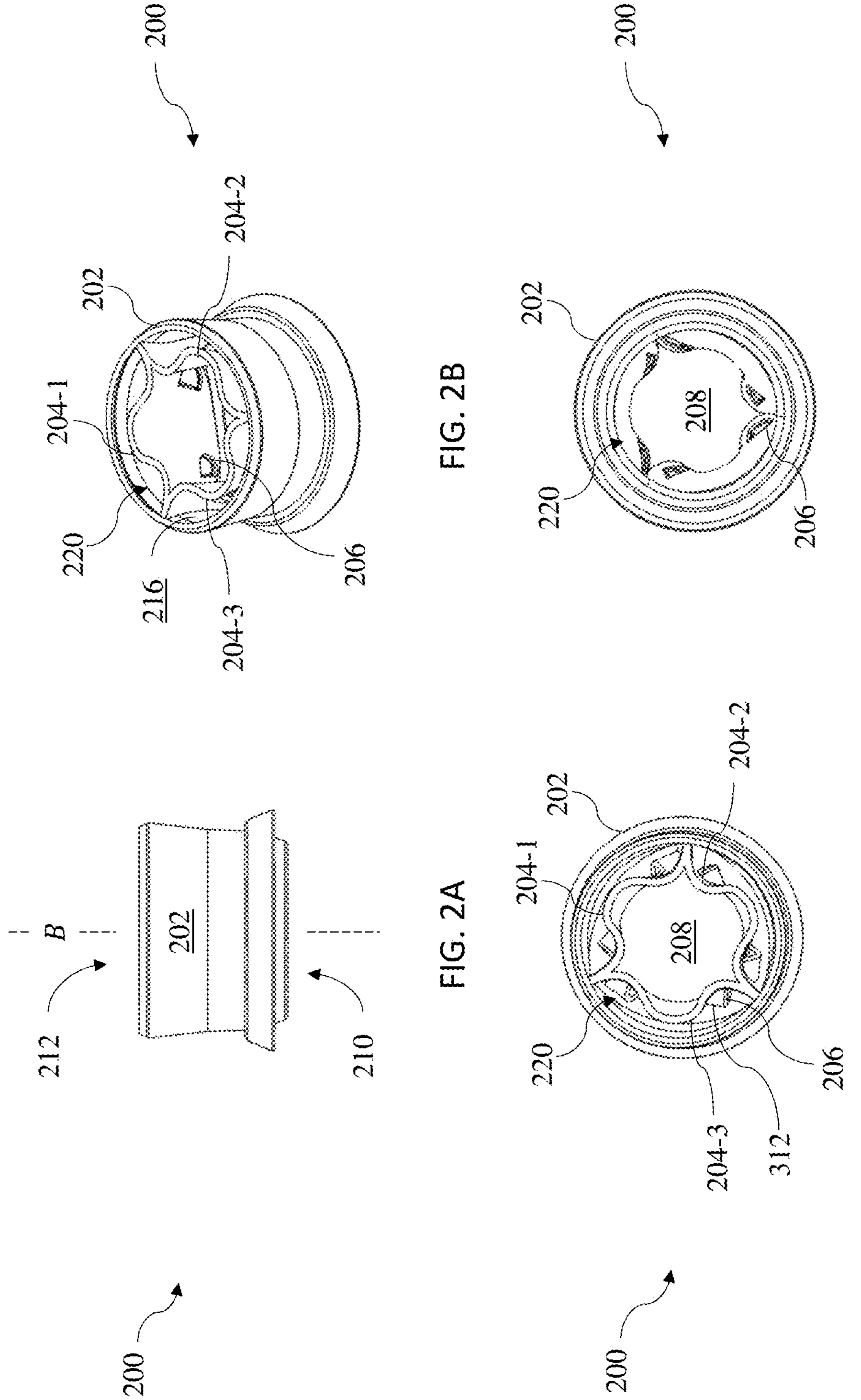
FIG. 2A, FIG. 2B, FIG. 2C, and FIG. 2D are top view, side view, perspective view, and bottom view simplified illustrations of an exemplary prosthetic heart valve, respectively, in accordance with some embodiments of the present invention.

According to some embodiments, and as described in greater detail elsewhere herein, the one or more openings 106/206/306 are positioned such that at an open position of the prosthetic heart valve, a portion of the blood flow is redirected from the passage 108/208 to one or more cavities 220 (or stagnation areas) formed between a heart tissue wall surface and the passage 108/208. According to some embodiments, such as depicted in FIG. 2B, the one or more cavities 220 are formed between the housing 202 and the one or more flaps 204. According to some embodiments, the one or more openings 106/206 are positioned such that the one or more cavities 220 are filled with redirected streams of blood during a heart cycle. Advantageously, filling the one or more cavities 220 with redirected blood flow at a predetermined rate and/or Reynolds number prevents stagnation of blood flow in the one or more cavities 220 and thus mitigates a risk of blood clot formation.

According to some embodiments, the one or more openings 106/206/306 are positioned along one or more location such that at an open position of the heart valve 100/200, a portion of the blood flow is redirected away from a main blood flow flowing through the passage 108/208. According to some embodiments, the redirected blood flow is directed along a longitudinal axis (A)/(B) of the passage 108/208, thereby reducing the volumetric flow rate of the main flow. According to some embodiments, the one or more openings 106/206/306 are sized and positioned such that the volumetric flow rate is below a predetermined threshold value associated with fluttering of the one or more flaps 104/204 throughout a heart cycle. According to some embodiments, the one or more openings 106/206/306 are positioned such that the blood flow is directed laminarly in a plurality of directions, thereby flushing one or more surfaced of the valve housing 102/202 and/or one or more flaps 104/204.

Figure 4:
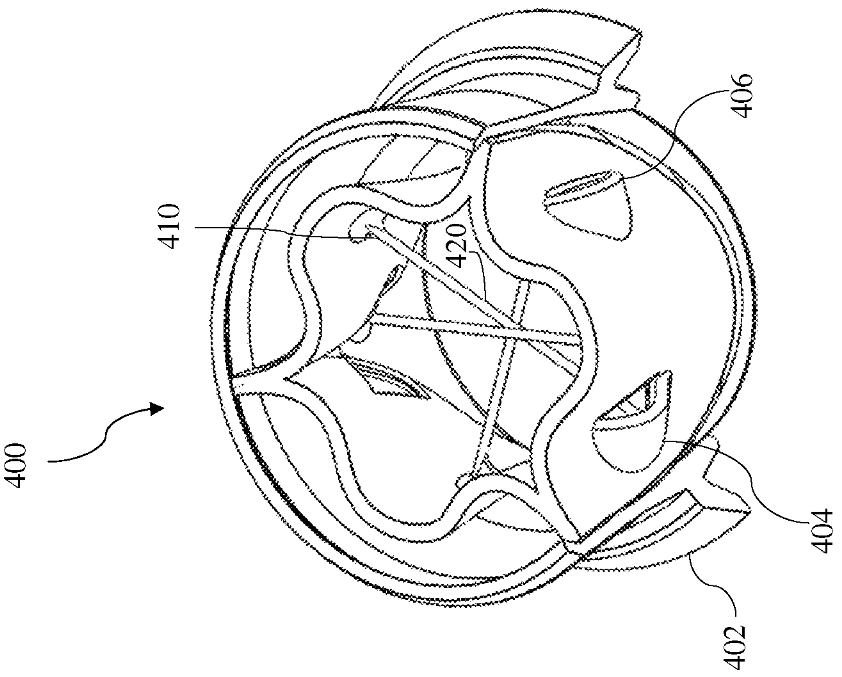
FIG. 4 is a perspective view with a cut-off section schematic illustrations of an exemplary prosthetic heart valve including one or more tethers, in accordance with some embodiments of the present invention.
Figure 5:
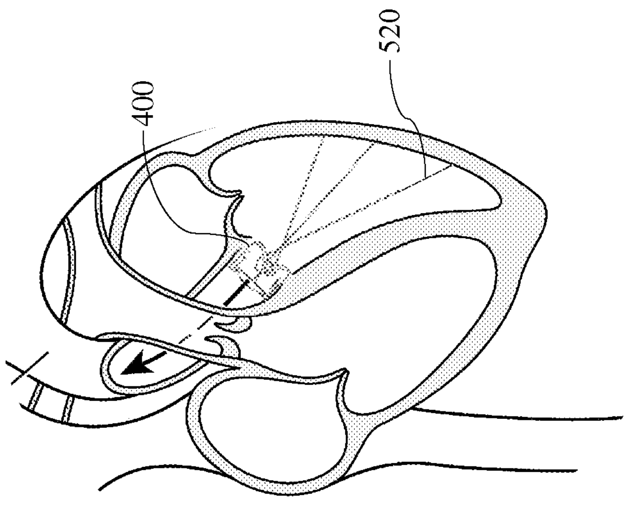
FIG. 5 is a side view schematic illustration of implementation of an exemplary prosthetic heart valve including one or more tethers, in accordance with some embodiments of the present invention.

Reference is made to FIG. 4, which is a perspective view with a cut-off section schematic illustrations of an exemplary prosthetic heart valve including one or more tethers, in accordance with some embodiments of the present invention, and to FIG. 5, which is a side view schematic illustration of implementation of an exemplary prosthetic heart valve including one or more tethers, in accordance with some embodiments of the present invention.

It is to be understood that the heart valve 400 as depicted in FIG. 4 has a cut-off section of the housing 402 in order to facilitate the viewing of the one or more flaps 404. According to some embodiments, the housing 402 may encircle and/or surround the one or more flaps 404.

According to some embodiments, the prosthetic heart valve 100/200/400 includes one or more tethers 420 configured to couple to at least one of the one or more flaps 104/204/404, the one or more openings 106/206/306/406, and the cardiac tissue of the subject. According to some embodiments, the one or more tethers 420 include a one or more wires, a string, and/or a rod. According to some embodiments, the one or more tethers 420 are flexible and/or semi-rigid.

According to some embodiments, the one or more tethers 420 are coupled to the one or more flaps 104/204/404 and/or the one or more openings 106/206/306/406 at a first end 410 of the tether 420. According to some embodiments, and as depicted in FIG. 4, the one or more tethers 420 are coupled to the one or more flaps 104/204/404 and/or the one or more openings 106/206/306/406 at a second end of the tether 420. According to some embodiments, and as depicted in FIG. 5, the one or more tethers 420/520 are coupled to the cardiac tissue of the subject at a second end of the tether 420/520. For example, according to some embodiments, and as depicted in FIG. 5, the second end 510 of the one or more tethers 420/520 is coupled to tissue of the left ventricle of the subject. According to some embodiments, the one or more tethers 420/520 are coupled to each other. According to some embodiments, the one or more tethers 420/520 are coupled to the valve housing 102/202. According to some embodiments, the one or more flaps 104/204/404 are coupled to the valve housing 102/202 and/or to another one of the one or more flaps 104/204/404 via the one or more tether 420/520.

A potential advantage of the one or more flaps 104/204/404 being coupled to the valve housing 102/202 and/or being coupled to another one of the one or more flaps 104/204/404 is in that the one or more layers 302 and/or a portion 308 of the layers 302 of the one or more flaps 104/204/404 are able to open in a radially inwards direction in relation to the rest of the flaps 104/204/404. According to some embodiments, the one or more layers 302 and/or a portion 308 of the layers 302 of the one or more flaps 104/204/404 are configured to extend radially inward such that the one or more openings 306 defined by the layers 302 includes an area larger than an opening in which the portion 308 of the layers 302 remains stationary.

According to some embodiments, each of the one or more openings 306 of the one or more flaps 104/204/404 are configured to open in relation to the body 320 of the flap 104/204/404 including the specific opening 306. According to some embodiments, one or more of the layers 302 are configured to move in relation to the body 320 of the flap 104/204/404.

A potential advantage of the one or more flaps 104/204/404 having a plurality of layers 302 is in that the layers 302 create a differential stiffness between the body 320 of the flap 104/204/404, thereby allowing the opening 306 to open towards the direction of the housing.

A potential advantage of the one or more flaps 104/204/404 being coupled to the valve housing 102/202 and/or being coupled to another one of the one or more flaps 104/204/404 using one or more tethers 420 is in that the one or more tethers 420 constrict the movement of the body 320 of the flap 104/204/404 while allowing the movement of the layers 302 to generate the openings 306. According to some embodiments, the one or more tethers 420 are configured to restrict a movement of the body 320 of the flap 104/204/404 to a distance essentially halfway towards the housing of the prosthetic valve, from a fully open position of the flap 104/204/404. According to some embodiments, the one or more tethers 420 are configured to restrict a movement of the body 320 of the flap 104/204/404 while the one or more openings 306 continue to open due to a movement of the one or more layers 302 in relation to the body 320 of the flap 104/204/404.

A potential advantage of the one or more flaps 104/204/404 being coupled to the cardiac tissue of the subject is in that the opening of the one or more openings 306 is synchronized with the heart cycle. According to some embodiments, during implementation of the heart valve 400, the motion during a heart cycle enables the adjustment of the one or more flaps 104/204/404 from a closed position of the heart valve 100/200/400 to an open position of the heart valve 100/200/400. According to some embodiments, during implementation of the heart valve 100/200/400, the one or more openings 306 are configured to open and close independently from the motion and/or adjustment of the one or more flaps 104/204/404.

Figure 6:
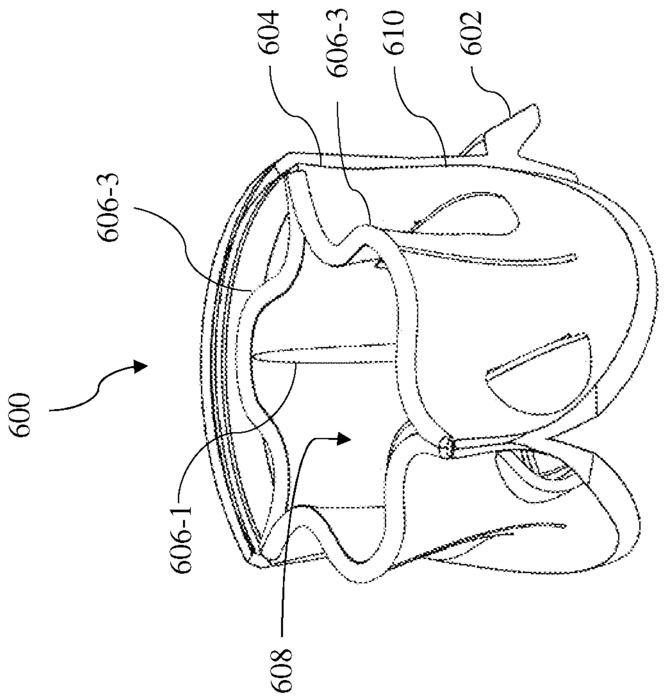
FIG. 6 is perspective view with a cut-off section schematic illustration of an exemplary prosthetic heart valve including one or more support members, in accordance with some embodiments of the present invention.

Reference is made to FIG. 6, which is perspective view with a cut-off section schematic illustration of an exemplary prosthetic heart valve, in accordance with some embodiments of the present invention. It is to be understood that the heart valve 600 as depicted in FIG. 6 has a cut-off section of the housing 602 in order to facilitate the viewing of the wall 610 of the flaps 604. According to some embodiments, the housing 602 may encircle and/or surround the wall 610 of the flaps 604.

According to some embodiments, the elasticity of different portions of the one or more flaps 104/204/404/604 varies. According to some embodiments, the elasticity of the different portions of the one or more flaps 104/204/404/604 varies due to variations in thickness and/or composition of the different portions of the one or more flaps 104/204/404/604. According to some embodiments, the one or more flaps 104/204/404/604 includes rigid and/or semi-rigid support members 606-1/606-2/606-3 (referred to herein as support members 606) positioned along the one or more flaps 104/204/404/604. According to some embodiments, the support members 606 are integral with the one or more flaps 104/204/404/604. According to some embodiments, the one or more support members 606 are positioned such that one or more areas of the flaps 104/204/404/604 are fortified in relation to the surrounding portions of the one or more flaps 104/204/404/604. According to some embodiments, the elasticity of the support members 606 is lower than the elasticity of a wall 610 of the one or more flaps 104/204/404/604. According to some embodiments, the thickness of the support members 606 is higher than the thickness of the wall 610.

According to some embodiments, the support members 606 include ribs such as ribs 606-1/606-2. According to some embodiments, the ribs 606-1/606-2 are positioned on an inner surface of the wall 610, an outer portion of the wall 610 and/or through a thickness of the wall 610. According to some embodiments, the support members include rims and/or shoulders 606-3 configured to outline a portion of the wall 610. According to some embodiments, the support members 606 are positioned parallel, angled, or perpendicular to a longitudinal axis of the passage 108/208/608.

A potential advantage of the one or more support members 606 is in that the wall 610 of the one or more flaps 104/204/404/604 is strengthened and/or re-enforced by the support members 606 thereby preventing the one or more flaps 104/204/404/604 from opening fully while enabling the one or more openings 106/206/306/406 to open due to pressure gradients of the blood flow within the heart.

A potential advantage of preventing the one or more flaps 104/204/404/604 from opening fully is in that it prevents the motion of the flap 104/204/404/604 from shutting the one or more openings 306 to a closed position due to inertial and drag forces. According to some embodiments, the motion of the body 320 of the flap 104/204/404/604 is limited such that when the body 320 of the flap 104/204/404/604 reaches a maximal distance, e.g., a distance from a fully open position to a semi-open position, the opening 306 is forced open by the inertia of the one or more layers 302 and/or the pressure gradient of the blood flow which applies force onto the one or more layers 302 of the opening 306.

A potential advantage of preventing the one or more flaps 104/204/404/604 from opening fully is in that about the support members 606 may prevent over closing and/or backflow flap collapse. According to some embodiments, the support members 606 can prevent the trembling of the flaps 104/204/404/604 at the fully opened position.

Figure 7B:
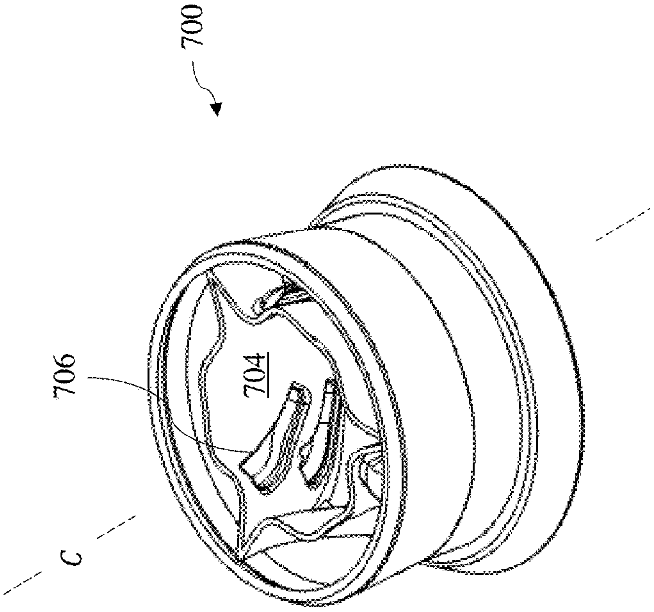
FIG. 7A and FIG. 7B are top view and perspective view simplified illustrations of an exemplary prosthetic heart valve, respectively, in accordance with some embodiments of the present invention.
Figure 7A:
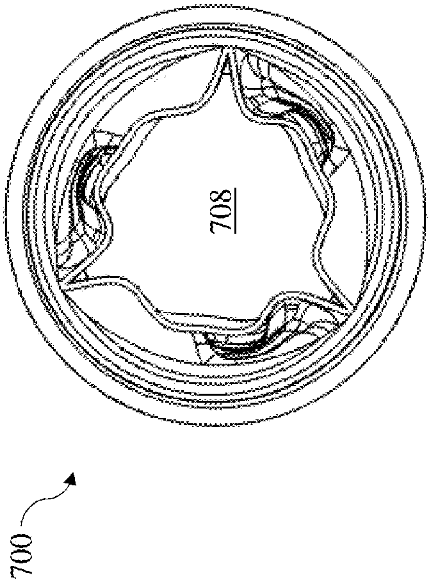

Reference is made to FIG. 7A and FIG. 7B, which are top view and perspective view simplified illustrations of an exemplary prosthetic heart valve, respectively, in accordance with some embodiments of the present invention. According to some embodiments, such as depicted in FIG. 7A and FIG. 7B, two or more of the one or more openings 106/206/306/406/706 are positioned consecutively along a length of the one or more flaps 104/204/404/604/704 parallel to the longitudinal axis (A)/(B)/(C) of the passage 108/208/608/708. According to some embodiments, the one or more openings 106/206/306/406/706 are equally spaced apart along a perimeter of the one or more flaps 704.

Reference is made to FIG. 8A, FIG. 8B, FIG. 8C, FIG. 8D and FIG. 8E, which are top view, side view, perspective view, bottom view, and cross-sectional view simplified illustrations of an exemplary prosthetic heart valve, respectively, in accordance with some embodiments of the present invention, to FIG. 9A, FIG. 9B, FIG. 9C, and FIG. 9D, which are top view, side view, perspective view, and bottom view simplified illustrations of an exemplary prosthetic heart valve, respectively, in accordance with some embodiments of the present invention, and to FIG. 10A, FIG. 10B, FIG. 10C, and FIG. 10D, which are top view, side view, perspective view, and bottom view simplified illustrations of an exemplary prosthetic heart valve, respectively, in accordance with some embodiments of the present invention.

According to some embodiments, such as depicted in FIG. 8A, FIG. 8B, FIG. 8C, FIG. 8D and FIG. 8E, the prosthetic heart valve includes a combination of rigid and flexible portion. According to some embodiments, such as depicted in FIG. 9A, FIG. 9B, FIG. 9C, and FIG. 9D, the prosthetic heart valve includes one or more reconstructed biological-like portions. According to some embodiments, the biological-like portions are included of biological materials. According to some embodiments, the biological-like portions include of a structure similar to a biological heart valve. For example, a biological-like flap may include a shape and elasticity of a biological leaflet of a human heart. According to some embodiments, such as depicted in FIG. 10A, FIG. 10B, FIG. 10C, and FIG. 10D, the prosthetic heart valve includes one or more biological-like portions including at least a portion of a flap. According to some embodiments, at least a portion of the one or more flaps include biological-like portions.

According to some embodiments, the one or more openings 106/206/306/406/706/806/906/1006 are positioned through the valve housing 102/202/802/902/1002 of the prosthetic heart valve 100/200/400/600/700/800/900/1002. According to some embodiments, a portion of the main blood flow entering the prosthetic heart valve 100/200/400/600/700/800/900/1000 at the inflow side 110/210/810/910/1010 is split into a plurality of streams by the one or more openings 106/206/306/406/706/806/906/1006 before reaching the outflow side 112/212/812/912/1012 of the prosthetic heart valve 100/200/400/600/700/800/900/1000.

According to some embodiments, such as depicted by FIG. 8A, FIG. 8B, FIG. 8C, FIG. 8D and FIG. 8E, the one or more flaps 104/204/404/604/704/804 are moveably coupled to the valve housing 102/202/802 such that the distance between the outer surfaces 816-1/816-2 of two of the one or more flaps 104/204/404/604/704/804 is smaller at an open position of the heart valve than at a closed position of the heart valve.

According to some embodiments, the one or more flaps 104/204/404/604/704/804 are moveably coupled to the valve housing 102/202/802 such that at an open position of the heart valve, at least a portion of the main blood flow entering the inflow side 810 of the heart valve is directed through the outflow side 812 of the heart valve and through a sub-passage 808-1/808-2 defined by the one or more flaps 104/204/404/604/704/804 and the passage 108/208/608/708/808.

According to some embodiments, the sub-passage 808-1/808-2 is configured to direct at least a portion of the main blood flow from the passage 808 and out of the prosthetic heart valve. According to some embodiments, the sub-passage 808-1/808-2 is configured to direct at least a portion of the main blood flow at a direction angled away from the longitudinal axis (D) of the passage 808. According to some embodiments, the sub-passages 808-1 and 808-2 are configured to direct at least a portion of the main blood flow at mirroring directions.

According to some embodiments, the heart valve 100/800/900/1000 includes a flange 118/818/918/1018 extending within the valve housing 102/802/902/1002. According to some embodiments, the flange 118/818/918/1018 is rigid, semi-rigid, and/or flexible. According to some embodiments, the flange 118/818/918/1018 is configured to further direct the blood flow exiting the heart valve, and, as described in greater detail elsewhere herein, provide control of the flow field surrounding the heart valve. According to some embodiments, the flange 118/818/918/1018 includes a cylindrical and/or conical shape. According to some embodiments, the flange 118/818/918/1018 extends out from the passage 808/908/1008.

Figure 8A:
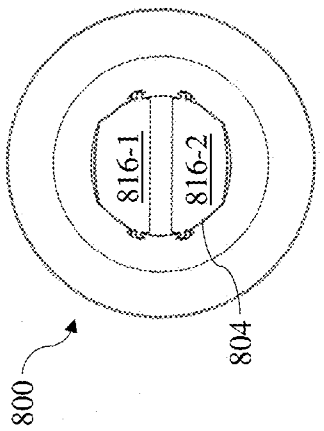
FIG. 8A, FIG. 8B, FIG. 8C, FIG. 8D and FIG. 8E are top view, side view, perspective view, bottom view, and cross-sectional view simplified illustrations of an exemplary prosthetic heart valve, respectively, in accordance with some embodiments of the present invention.
Figure 8B:
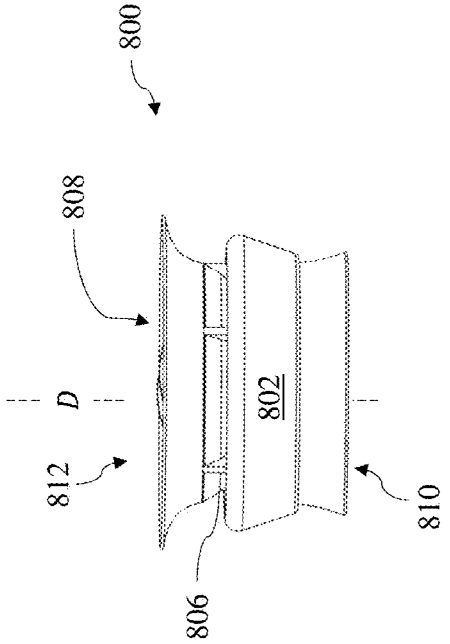
Figure 8C:
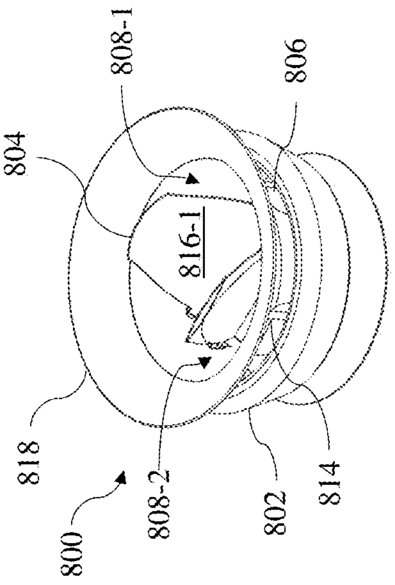
Figure 8D:
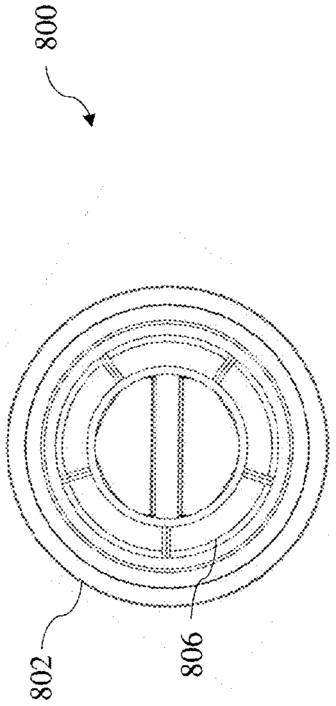
Figure 8E:
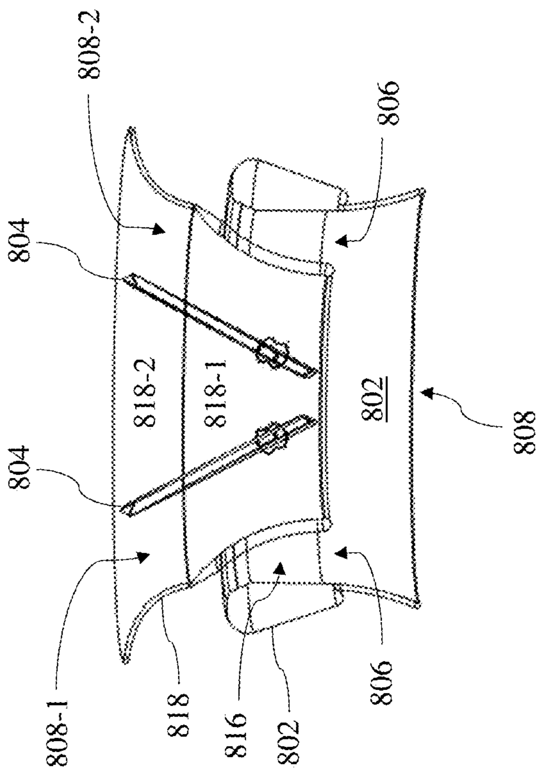
Figure 9A:
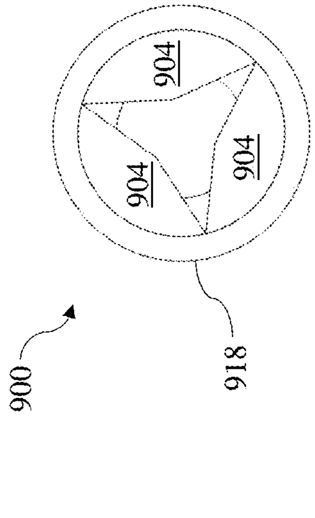
FIG. 9A, FIG. 9B, FIG. 9C, and FIG. 9D are top view, side view, perspective view, and bottom view simplified illustrations of an exemplary prosthetic heart valve, respectively, in accordance with some embodiments of the present invention.
Figure 9B:
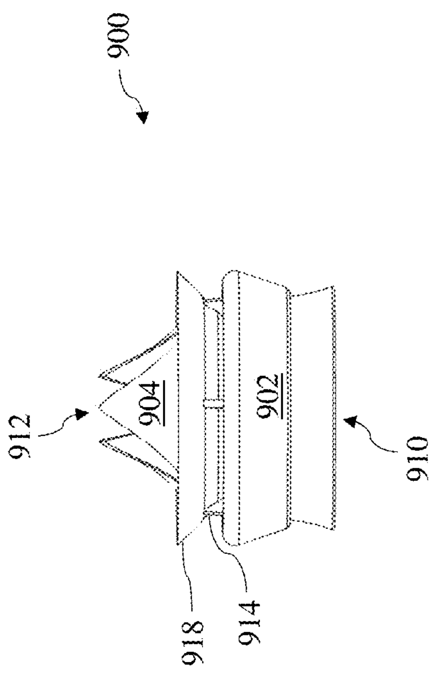
Figure 9C:
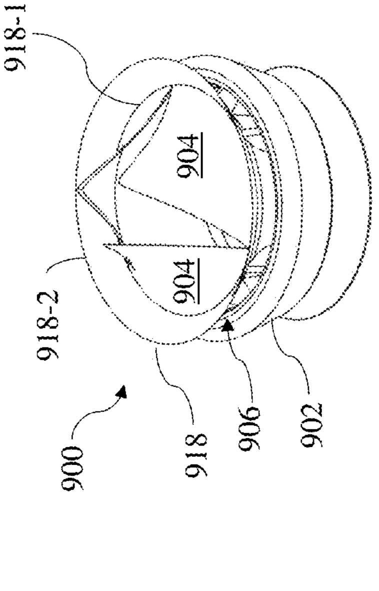
Figure 9D:
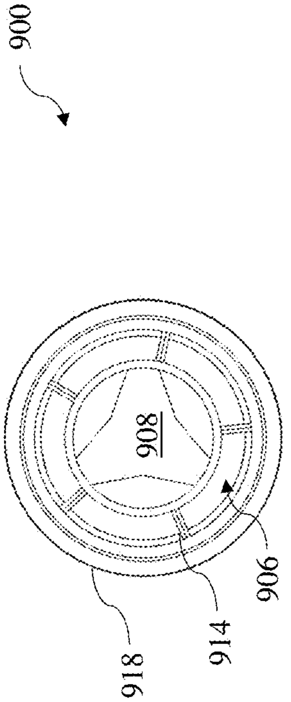
Figures 10A, 10B, 10C, 10D:
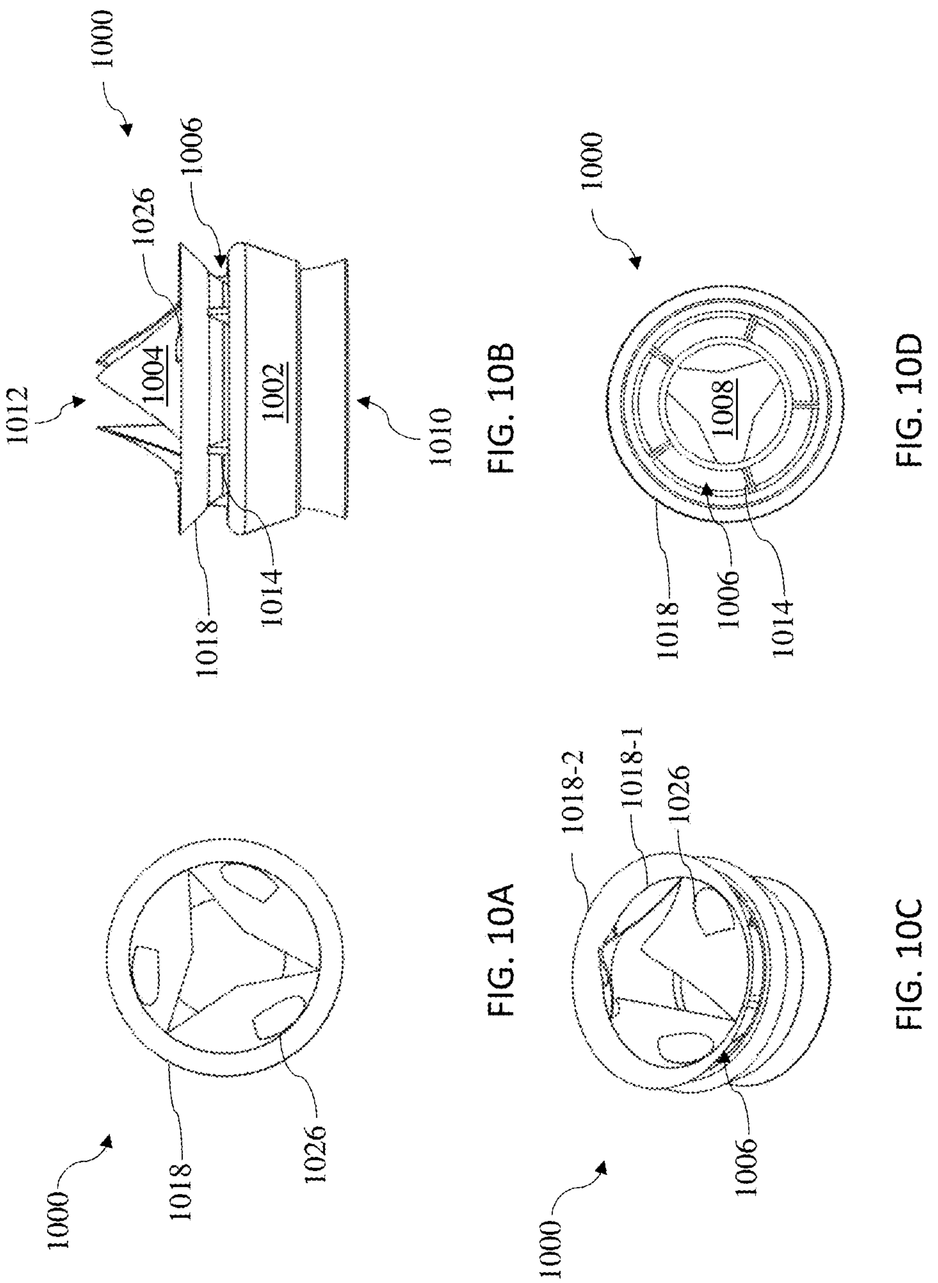
FIG. 10A, FIG. 10B, FIG. 10C, and FIG. 10D are top view, side view, perspective view, and bottom view simplified illustrations of an exemplary prosthetic heart valve, respectively, in accordance with some embodiments of the present invention.

According to some embodiments, and as depicted in FIG. 8E, the one or more openings 806/906/1006 encircle a perimeter of the valve housing. According to some embodiments, the one or more openings 806/906/1006 are defined by the gap between the passage 808/908/1008 and the flange 818/918/1018. According to some embodiments, the one or more openings 806/906/1006 are defined by the gap between the wall surrounding the passage 808/908/1008 (or the wall of the passage) and the flange 818/918/1018. According to some embodiments, the gap between the wall of the passage 808/908/1008 and the flange 818/918/1018 extends circumferentially around the flange 818/918/1018 and/or within the passage 808/908/1008. According to some embodiments, the heart valve includes one or more columns 814/914/1014 coupled to the flange at one end of the column 814/914/1014 and to the valve housing 802/902/1002 at a second end thereof.

A potential advantage of the one or more openings 806/906/1006 is in that the gap between (the wall of) the passage 808/908/1008 and the flange 818/918/1018 further defines a sub-passage 808-1/808-2 there between. Advantageously, according to some embodiments, the sub-passage 808-1/808-2 is configured to further direct the blood flow exiting the heart valve, and, as described in greater detail elsewhere herein, provide control of the flow field surrounding the heart valve.

According to some embodiments, the flange 818/918/1018 includes an inner portion 818-1/918-1/1018-1 and an outer portion 818-2/918-2/1018-2. According to some embodiments, the elasticity of the outer portion 818-2/918-2/1018-2 is higher than the elasticity of the inner portion 818-1/918-1/1018-1. According to some embodiments, the outer portion 818-2/918-2/1018-2 includes a plurality of additional flaps.

Figure 11:
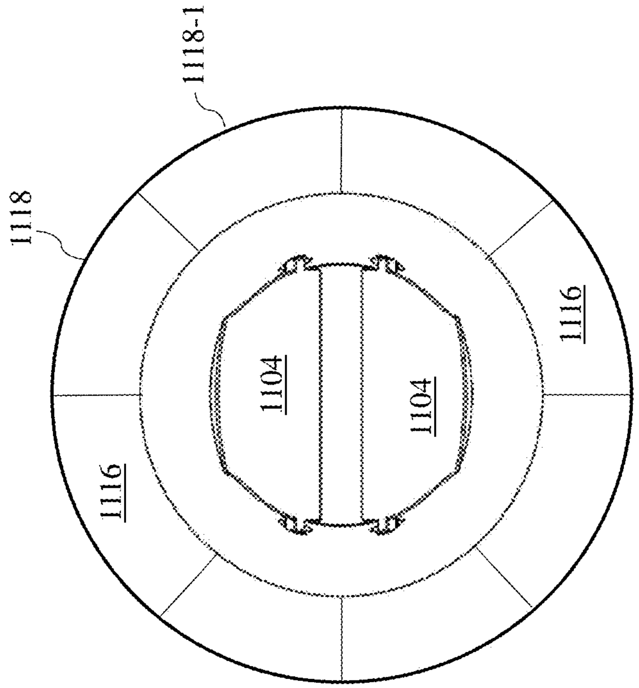
FIG. 11 is a top view simplified illustration of an exemplary prosthetic heart valve, in accordance with some embodiments of the present invention.

Reference is made to FIG. 11, which is a top view simplified illustration of an exemplary prosthetic heart valve, in accordance with some embodiments of the present invention. According to some embodiments, such as depicted by FIG. 11, the flange 1118 and the outer portion 1118-1 of the flange 1118 includes a plurality of additional flaps 1116. According to some embodiments, the outer portion 1118-1 of the flange 1118 is split into a plurality of additional flaps 1116. According to some embodiments, the plurality of additional flaps 1116 surround at least a portion of the one or more flaps 104/204/404/604/704/804/904/1004/1104.

According to some embodiments, and as depicted in FIG. 10A, FIG. 10B, FIG. 10C, and FIG. 10D, the prosthetic heart valve includes a combination of one or more openings 1006 defined by the gap between the passage 1008 and the flange 1018, and one or more openings 1026 positioned along the one or more flaps 1104 of the prosthetic heart valve 1000.

Figure 12B:
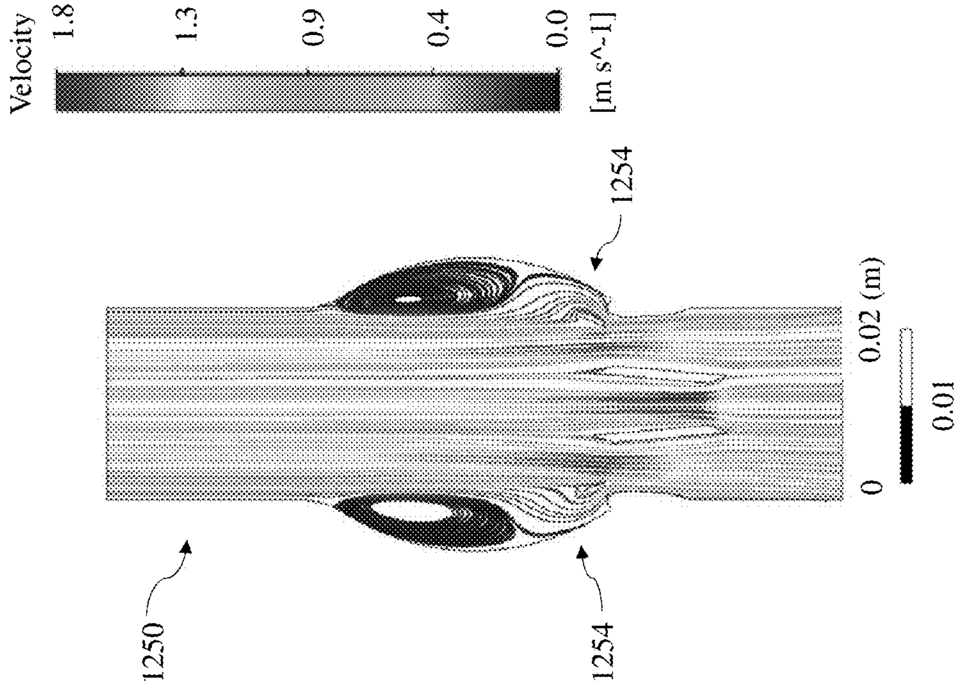
FIG. 12A and FIG. 12B are cross sectional simplified illustrations of a flow simulation using a heart valve without openings and an exemplary prosthetic heart valve with openings, respectively, during a simulation of an implementation, in accordance with some embodiments of the present invention.
Figure 12A:
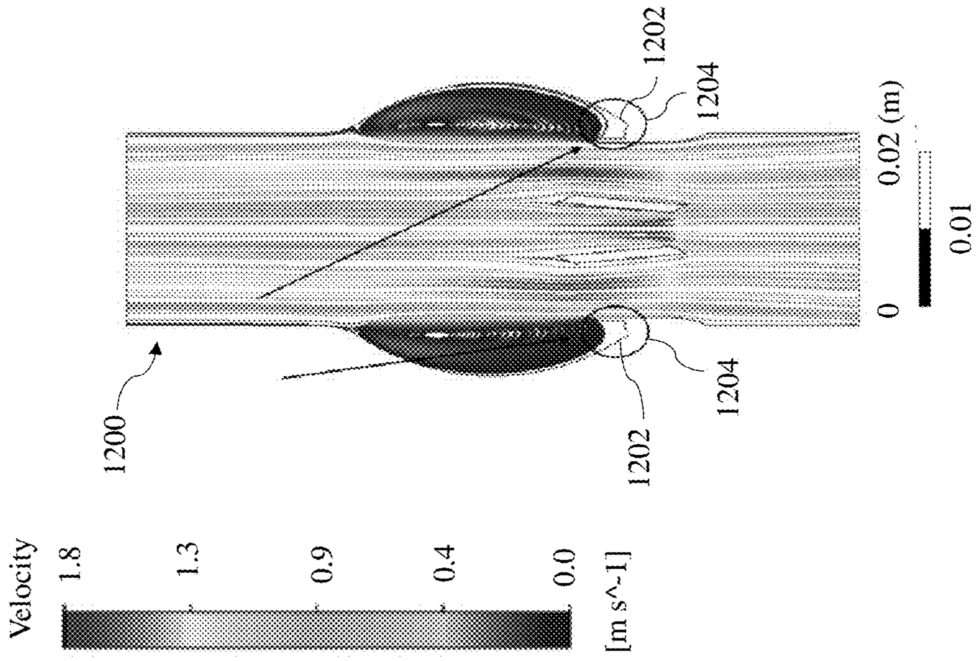

Reference is made to FIG. 12A and FIG. 12B, which are cross sectional simplified illustrations of a flow simulation using a heart valve without openings and an exemplary prosthetic heart valve with openings, respectively, during a simulation of an implementation, in accordance with some embodiments of the present invention.

According to some embodiments, the flow field 1200 of FIG. 12A includes cavities 1202 formed between the heart valve and the tissue wall at stagnation area 1204. According to some embodiments, the cavity 1202 and/or stagnation area 1204 includes no blood flow flowing therethrough.

According to some embodiments, the flow field 1250 of FIG. 12B includes blood flow in the stagnation area 1254. According to some embodiments, the blood flow in the stagnation area 1254 is laminar. The stagnation area 1254 is positioned in the same location as stagnation area 1204 of FIG. 12A, in relation to the heart valve and/or the tissue wall. The flow field 1250 depicted in FIG. 12B is an exemplary flow field generated by implementation of a heart valve including one or more openings, for example, such as, heart valves 100/200/400/600/700/800/900/1000/1100 as described in greater detail elsewhere herein.

Figure 13B:
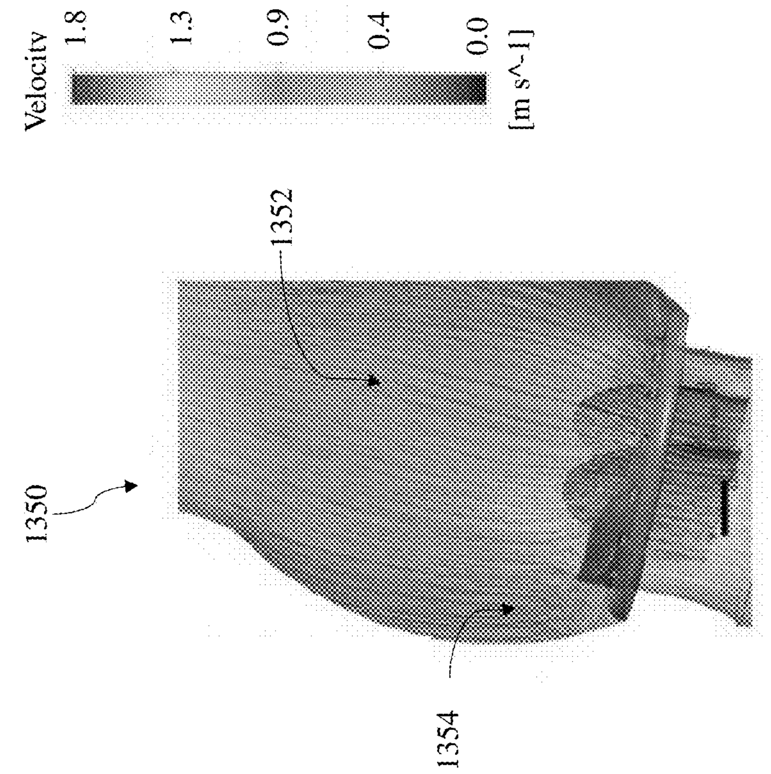
FIG. 13A and FIG. 13B are side view simplified illustrations of a flow simulation using a heart valve without openings and an exemplary prosthetic heart valve with openings, respectively, during a simulation of an implementation, in accordance with some embodiments of the present invention.
Figure 13A:
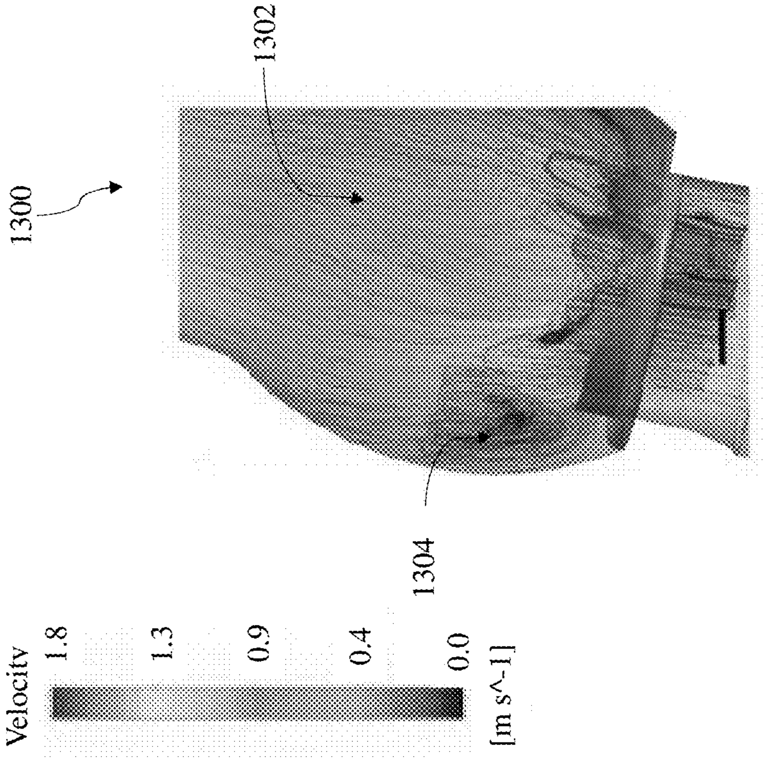

Reference is made to FIG. 13A and FIG. 13B, which are side view simplified illustrations of a flow simulation using a heart valve without openings and an exemplary prosthetic heart valve with openings, respectively, during a simulation of an implementation, in accordance with some embodiments of the present invention.

The flow field 1300 depicted in FIG. 13A includes slow recirculation and stagnation (in the middle) flow formed between the heart valve and the tissue wall at stagnation area 1304. According to some embodiments, the recirculation flow of stagnation area 1304 is caused due to a gradient of pressure which is formed by a high flow rate in areas surrounding stagnation area 1304 and low and/or non-existent flow rate within the stagnation area 1304.

According to some embodiments, the flow field 1350 of FIG. 13B includes blood flow streaming into the stagnation area 1354 from the one or more openings of the heart valve. According to some embodiments, the blood flow streaming into the stagnation area 1354 from the one or more openings of the heart valve is laminar. The stagnation area 1354 is positioned in the same location as stagnation area 1304 of FIG. 13A, in relation to the heart valve and/or the tissue wall.

The flow field 1300 depicted in FIG. 13A includes slow recirculating flow formed within the main blood stream exiting the outflow side of the heart valve at area 1302.

According to some embodiments, the flow field 1350 of FIG. 13B includes laminar blood flow streaming into the area 1352 from the outflow side of the heart valve. According to some embodiments, the blood flow streaming into the stagnation area 1354 is laminar due to a lowering of the volumetric flow rate of the main flow exiting the outflow side. According to some embodiments, the volumetric flow rate is lowered by the redirected streams of blood exiting the heart valve through the one or more openings. The stagnation area 1354 is located in the same location as stagnation area 1304 of FIG. 13A, in relation to the heart valve and/or the tissue wall.

The flow field 1350 depicted in FIG. 13B is an exemplary flow field generated by implementation of a heart valve including one or more openings, for example, such as, heart valves 100/200/400/600/700/800/900/1000/1100 as described in greater detail elsewhere herein.

Figures 14A, 14B:
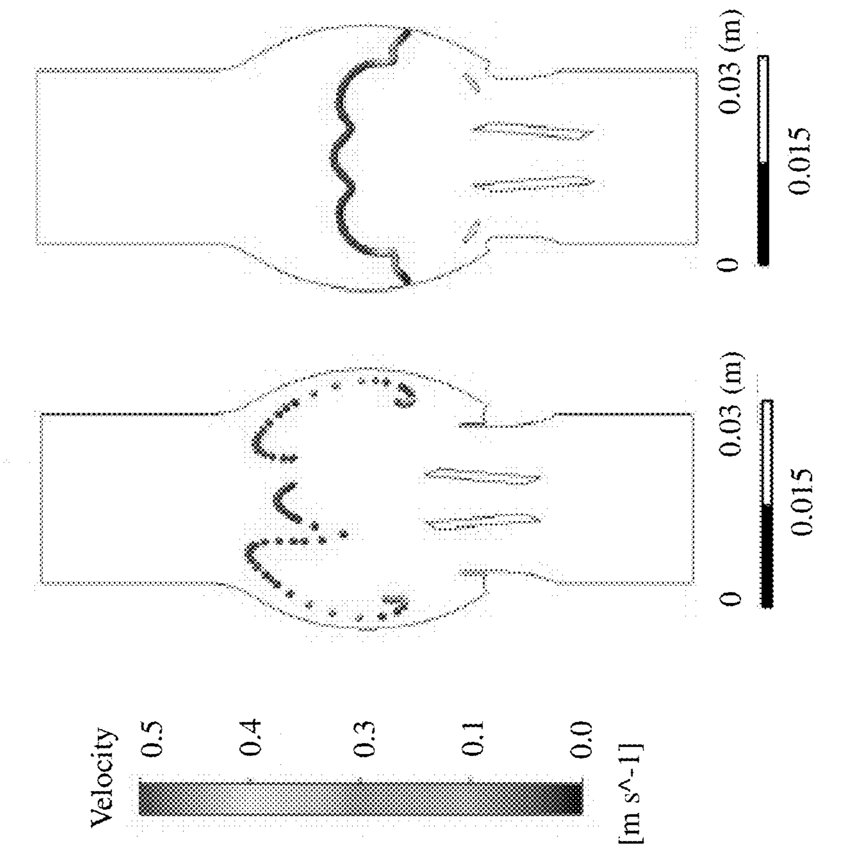
FIG. 14A and FIG. 14B are cross sectional simplified illustrations of a flow simulation using a heart valve without openings and an exemplary prosthetic heart valve with openings, respectively, at t=0.12 [sec], in accordance with some embodiments of the present invention.
Figures 15A, 15B:
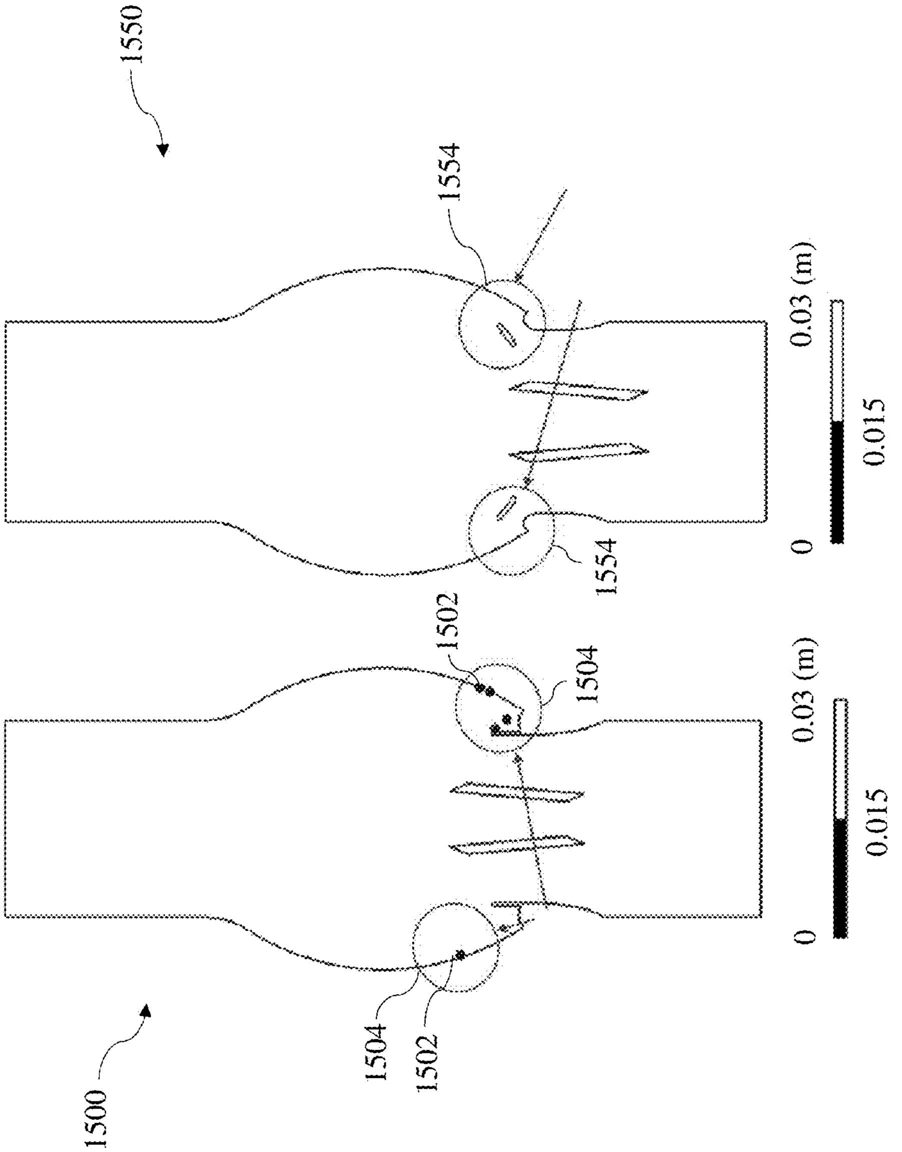
FIG. 15A and FIG. 15B are cross sectional simplified illustrations of a flow simulation using a heart valve without openings and an exemplary prosthetic heart valve with openings, respectively, at t=1.12 [sec], in accordance with some embodiments of the present invention.

Reference is made to FIG. 14A and FIG. 14B, which are cross sectional simplified illustrations of a flow simulation using a heart valve without openings and an exemplary prosthetic heart valve with openings, respectively, at t=0.12 [sec], in accordance with some embodiments of the present invention, and to FIG. 15A and FIG. 15B, which are cross sectional simplified illustrations of a flow simulation using a heart valve without openings and an exemplary prosthetic heart valve with openings, respectively, at t=1.12 [sec], in accordance with some embodiments of the present invention.

FIG. 14A depicts a flow filed 1400 of a prosthetic heart valve including no openings. FIG. 15A shows the adhered particles which remain on the same prosthetic heart valve after 1.12 seconds of the heart cycle.

FIG. 15A shows the adhered particles 1502 on the prosthetic heart valve having no openings, in the circumferential (stagnation) area 1504 of the prosthetic heart valve. FIG. 15B shows a same circumferential (stagnation) area 1554 of an exemplary prosthetic heart valve with one or more openings, wherein the circumferential (stagnation) area 1554 includes no adhered particles. The exemplary heart valve prevents interruption of blood flow and/or stasis within the circumferential (stagnation) areas 1504/1554. The area 1454 is positioned in the same location as (stagnation) area 1504 of FIG. 15A, in relation to the heart valve and/or the tissue wall.

Figures 16A, 16B:
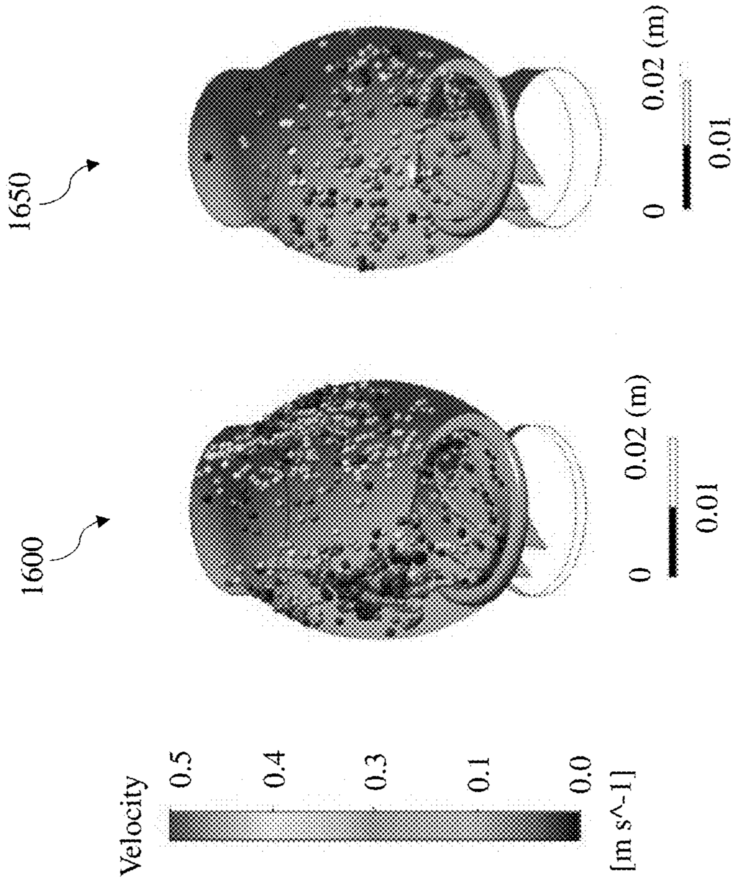
FIG. 16A and FIG. 16B are side view simplified illustrations of a flow simulation using a heart valve without openings and an exemplary prosthetic heart valve with openings, respectively, at t=0.12 [sec], in accordance with some embodiments of the present invention.
Figure 17A:
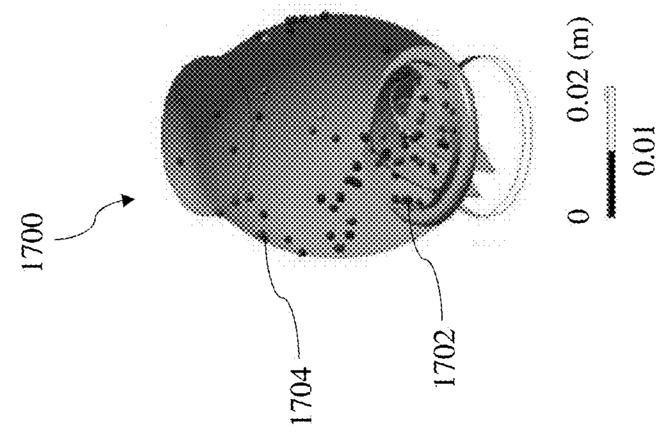
FIG. 17A and FIG. 17B are side view simplified illustrations of a flow simulation using a heart valve without openings and an exemplary prosthetic heart valve with openings, respectively, at t=1.12 [sec], in accordance with some embodiments of the present invention.
Figure 17B:
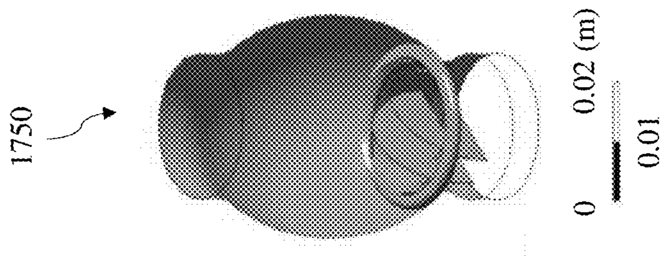

Reference is made to FIG. 16A and FIG. 16B, which are side view simplified illustrations of a flow simulation using a heart valve without openings and an exemplary prosthetic heart valve with openings, respectively, at t=0.12 [sec], in accordance with some embodiments of the present invention, and to FIG. 17A and FIG. 17B, which are side view simplified illustrations of a flow simulation using a heart valve without openings and an exemplary prosthetic heart valve with openings, respectively, at t=1.12 [sec], in accordance with some embodiments of the present invention.

FIG. 17A shows a flow field 1700 including adhered particles 1702 on the prosthetic heart valve having no openings, and stagnation of the particles 1704 surrounding the prosthetic heart valve. FIG. 17B shows a flow field 1750 of an exemplary prosthetic heart valve with one or more openings, wherein the flow field 1750 includes no adhered particles. The exemplary heart valve depicted by FIG. 17B prevents interruption of blood flow and/or stasis.

Figure 18B:
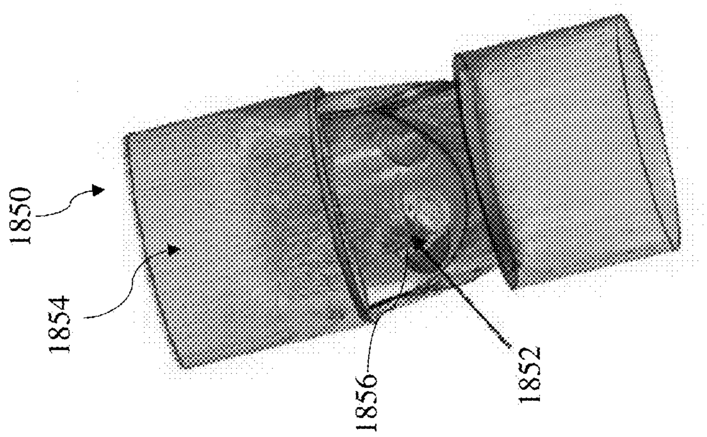
FIG. 18A and FIG. 18B are side view simplified illustrations of a flow simulation using a heart valve without openings and an exemplary prosthetic heart valve with openings, respectively, in accordance with some embodiments of the present invention.
Figure 18A:
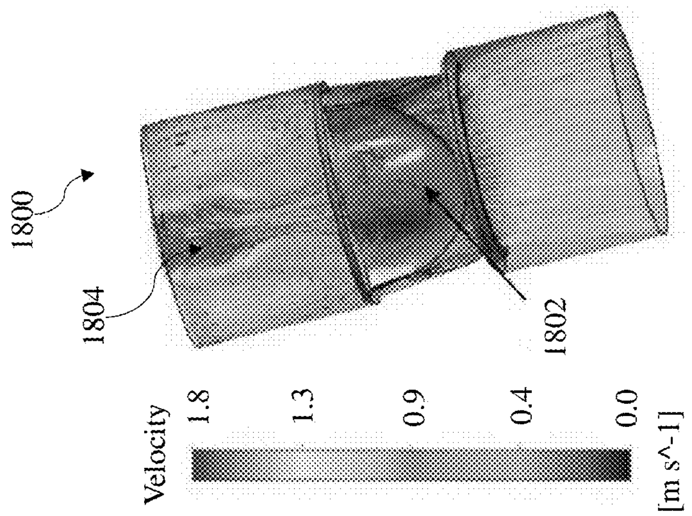

Reference is made to FIG. 18A and FIG. 18B, which are side view simplified illustrations of a flow simulation using a heart valve without openings and an exemplary prosthetic heart valve with openings, respectively, in accordance with some embodiments of the present invention.

FIG. 18A shows a flow field 1800 of the prosthetic heart valve having no openings in which slow recirculating flow 1802 is visible within portions of the prosthetic heart valve. FIG. 18B shows a flow field 1850 of an exemplary prosthetic heart valve with one or more openings, wherein the flow field 1850 includes faster recirculating flows or no recirculation flow. The flow field 1850 is laminar in the areas surrounding the openings 1856 of the heart valve. A comparison between the flow field 1800 and flow field 1850 shows a reduction of the volumetric flow rate within the area 1854 of FIG. 18B in relation to the area 1804 of FIG. 18A.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "include" "comprise" and "have", and forms thereof, are not necessarily limited to members in a list with which the words may be associated. In addition, where there are inconsistencies between this application and any document incorporated by reference, it is hereby intended that the present application controls.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A prosthetic heart valve, comprising: a valve housing configured to be positioned adjacent to a heart valve annulus; one or more flaps moveably coupled to said valve housing; a passage defined by an inner surface of said valve housing and/or said one or more flaps, wherein said passage is configured to facilitate blood flow therethrough along a longitudinal axis thereof, from an inflow side to an outflow side of said valve; one or more openings through said inner surface, the one or more openings being located such that at an open position of the heart valve, a portion of the blood flow flowing along the longitudinal axis of said passage is redirected from said passage through said one or more openings, wherein each of the openings is configured to direct blood flowing therethrough in a circumferential direction about the valve housing that defines the passage and/or about the one or more flaps that defines the passage, thereby mitigating stagnation of the blood flow and thus mitigating a risk of blood clots formation; and one or more sub-passages located between said one or more openings and said outflow side of said heart valve, wherein said one or more of said sub-passages are structured to further redirect a blood flow from said one or more openings.

2. The prosthetic heart valve according to claim 1, wherein said flaps are bioprosthetic/bioprosthetic-like.

3. The prosthetic heart valve according to claim 1, wherein said one or more openings are positioned such that at an open position, a portion of the blood flow is redirected from said passage to a cavity formed between a heart tissue wall surface and said passage.

4. The prosthetic heart valve according to claim 1, wherein said one or more openings are positioned such that the blood flow is directed laminarly in a plurality of directions, thereby flushing one or more surfaces of the valve housing and/or one or more flaps.

5. The prosthetic heart valve according to claim 1, wherein said one or more openings are positioned such that the blood flow is directed laterally in relation to a cross-sectional plane of the passage.

6. The prosthetic heart valve according to claim 1, wherein said one or more openings are positioned such as to facilitate backflow of blood through said one or more openings and thereby facilitate flushing blood through the one or more openings when the flaps are at least partially closed.

7. The prosthetic heart valve according to claim 1, wherein said one or more openings are sized and positioned such as to define a predetermined flow field surrounding said heart valve during each phase of the heart cycle.

8. A prosthetic heart valve, comprising: a valve housing configured to be positioned adjacent to a heart valve annulus; one or more flaps moveably coupled to said valve housing; a passage defined by an inner surface of said valve housing and/or said one or more flaps, wherein said passage is configured to facilitate blood flow therethrough along a longitudinal axis thereof, from an inflow side to an outflow side of said valve; one or more openings through said inner surface, the one or more openings being located such that at an open position of the heart valve, a portion of the blood flow flowing along the longitudinal axis of said passage is redirected from said passage through said one or more openings, wherein each of the openings is configured to direct blood flowing therethrough in a circumferential direction about the valve housing that defines the passage and/or about the one or more flaps that defines the passage, thereby mitigating stagnation of the blood flow and thus mitigating a risk of blood clots formation; and at least one support member positioned along at least a portion of the one or more flaps, wherein an elasticity of the support member is lower than an elasticity of the one or more flaps, wherein said support member is positioned along at least a section of a perimeter of the one or more flaps.

9. A prosthetic heart valve, comprising: a valve housing configured to be positioned adjacent to a heart valve annulus; one or more flaps moveably coupled to said valve housing; a passage defined by an inner surface of said valve housing and/or said one or more flaps, wherein said passage is configured to facilitate blood flow therethrough along a longitudinal axis thereof, from an inflow side to an outflow side of said valve; one or more openings through said inner surface, the one or more openings being located such that at an open position of the heart valve, a portion of the blood flow flowing along the longitudinal axis of said passage is redirected from said passage through said one or more openings, wherein each of the openings is configured to direct blood flowing therethrough in a circumferential direction about the valve housing that defines the passage and/or about the one or more flaps that defines the passage, thereby mitigating stagnation of the blood flow and thus mitigating a risk of blood clots formation; and at least one tether coupled at a first end thereof to at least one flap.

10. The prosthetic heart valve according to claim 9, wherein a second end of said tether is configured to couple to a cardiac tissue of the subject or to a second flap.

11. The prosthetic heart valve according to claim 1, wherein said one or more openings are sized and positioned in said inner surface such that said redirected blood flow has a Reynolds number below a predetermined threshold value associated with preventing turbulence and thereby preventing or mitigating fluttering of said one or more flaps.

12. The prosthetic heart valve according to claim 1, wherein said one or more openings are sized and positioned in said inner surface such that a main blood flow and said redirected blood flow have a Reynolds number below a predetermined threshold value throughout the heart cycle.

13. The prosthetic heart valve according to claim 1, wherein said one or more openings are sized and positioned in said inner surface such that a shear stress accumulated on said valve housing is below a predetermined threshold value associated with platelet shear activation and/or hemolysis.

* * * * *